US009512151B2

(12) United States Patent
Litz et al.

(10) Patent No.: US 9,512,151 B2
(45) Date of Patent: Dec. 6, 2016

(54) PRODUCT CONTAINING MONOMER AND POLYMERS OF TITANYLS AND METHODS FOR MAKING SAME

(75) Inventors: Kyle E. Litz, Ballston Spa, NY (US); Partha Dutta, Clifton Park, NY (US); Sarah Lewis, Delmar, NY (US); Mark Rossetti, Castleton, NY (US); James Pawlson, Averill Park, NY (US); Timothy Ullman, Averill Park, NY (US); Giyana Amaratunga, Clifton Park, NY (US); Jennifer L. Vreeland, Troy, NY (US); Tracey M. Jordan, Delmar, NY (US)

(73) Assignee: AUTERRA, INC., Schenectady, NY (US)

( * ) Notice: Subject to any disclaimer, the term of this patent is extended or adjusted under 35 U.S.C. 154(b) by 964 days.

(21) Appl. No.: 12/598,474

(22) PCT Filed: May 2, 2008

(86) PCT No.: PCT/US2008/005624
§ 371 (c)(1),
(2), (4) Date: Apr. 23, 2010

(87) PCT Pub. No.: WO2008/153633
PCT Pub. Date: Dec. 18, 2008

(65) Prior Publication Data
US 2011/0119988 A1    May 26, 2011

Related U.S. Application Data

(60) Provisional application No. 60/924,214, filed on May 3, 2007, provisional application No. 60/917,171, filed on May 10, 2007, provisional application No. 61/039,619, filed on Mar. 26, 2008.

(51) Int. Cl.
*C01G 23/00* (2006.01)
*C01G 25/00* (2006.01)
(Continued)

(52) U.S. Cl.
CPC .................................. *C07F 7/006* (2013.01)

(58) Field of Classification Search
CPC .... C07F 7/006; B01J 31/223; B01J 2531/46; C08G 79/00

USPC .............................................. 44/300; 556/54
See application file for complete search history.

(56) References Cited

U.S. PATENT DOCUMENTS 2,764,525 A    9/1956    Porter et al.
2,789,134 A    4/1957    Nelson et al.
(Continued)

FOREIGN PATENT DOCUMENTS

FR    1299736 A    7/1962
WO    0181715 A2    11/2001
(Continued)

OTHER PUBLICATIONS

Written Opinion and International Search Report from prior PCT/US2008/005624 mailed May 26, 2009, 15 pages.
(Continued)

*Primary Examiner* — Ellen McAvoy
*Assistant Examiner* — Ming Cheung Po
(74) *Attorney, Agent, or Firm* — Schmeiser, Olsen & Watts, LLP

(57) ABSTRACT

A compound of Formula (II) and (III), or a mixture of any two or more thereof; wherein M is Ti or Zr; $R^3$ at each occurrence is H, F, Cl, Br, I, CN, $OR^4$, $NR^5R^6$, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; $R^4$ is H, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; $R^5$ and $R^6$ are independently H, substituted or unsubstituted alkyl, substituted or unsubstituted cycloalkyl, substituted or unsubstituted heterocyclylalkyl, or $R^5$ and $R^6$ may join to form a heterocyclic ring containing the N to which they are attached; and n'=0-4. Such compounds form optically transparent and/or clear films or particles or may be used to prepare such materials.

6 Claims, 6 Drawing Sheets

(51) Int. Cl.
*C01G 27/00* (2006.01)
*C07F 7/00* (2006.01)

(56) References Cited

U.S. PATENT DOCUMENTS

| | | | |
|---|---|---|---|
| 2,910,434 A | 10/1959 | Hess et al. | |
| 2,987,470 A | 6/1961 | Turken | |
| 3,136,714 A | 6/1964 | Gibson et al. | |
| 3,164,545 A | 1/1965 | Mattox | |
| 3,505,210 A | 4/1970 | Wallace et al. | |
| 3,558,747 A | 1/1971 | Meltsner | |
| 3,565,793 A | 2/1971 | Herbstman et al. | |
| 3,668,117 A | 6/1972 | Patel et al. | |
| 3,819,509 A | 6/1974 | Wolk et al. | |
| 3,847,797 A | 11/1974 | Pasternak et al. | |
| 3,926,604 A | 12/1975 | Smay et al. | |
| 3,945,914 A | 3/1976 | Yoo et al. | |
| 3,948,759 A | 4/1976 | King et al. | |
| 3,957,620 A | 5/1976 | Fukui et al. | |
| 3,960,706 A | 6/1976 | McCollum | |
| 3,960,708 A | 6/1976 | McCollum | |
| 3,964,995 A | 6/1976 | Wolk et al. | |
| 4,003,823 A | 1/1977 | Baird et al. | |
| 4,119,528 A | 10/1978 | Baird, Jr. et al. | |
| 4,127,470 A | 11/1978 | Baird, Jr. et al. | |
| 4,192,736 A | 3/1980 | Kluksdahl | |
| 4,224,140 A | 9/1980 | Fujimori et al. | |
| 4,374,949 A | 2/1983 | Massey et al. | |
| 4,437,980 A | 3/1984 | Heredy et al. | |
| 4,444,655 A | 4/1984 | Shiroto et al. | |
| 4,591,426 A | 5/1986 | Krasuk et al. | |
| 4,645,589 A | 2/1987 | Krambeck et al. | |
| 4,665,261 A | 5/1987 | Mazurek | |
| 4,923,682 A * | 5/1990 | Roberts et al. | 423/611 |
| 4,944,936 A | 7/1990 | Lawhorne | |
| 5,009,876 A | 4/1991 | Hennings et al. | |
| 5,064,523 A | 11/1991 | Kretschmar et al. | |
| 5,089,149 A | 2/1992 | Ridland et al. | |
| 5,166,118 A | 11/1992 | Kretschmar et al. | |
| 5,288,681 A | 2/1994 | Gatsis | |
| 5,616,751 A * | 4/1997 | Nakai | B01J 31/2226 556/54 |
| 5,637,739 A | 6/1997 | Jacobsen et al. | |
| 5,783,165 A | 7/1998 | Wilson et al. | |
| 6,001,326 A | 12/1999 | Kim et al. | |
| 6,087,662 A | 7/2000 | Wilt et al. | |
| 6,160,193 A | 12/2000 | Gore | |
| 6,245,223 B1 | 6/2001 | Gorbaty et al. | |
| 6,368,495 B1 | 4/2002 | Kocal et al. | |
| 6,403,526 B1 | 6/2002 | Lussier et al. | |
| 6,406,616 B1 | 6/2002 | Rappas et al. | |
| 6,471,852 B1 | 10/2002 | Mark et al. | |
| 6,544,409 B2 | 4/2003 | DeSouza | |
| 6,547,957 B1 | 4/2003 | Sudhakar et al. | |
| 6,562,312 B2 | 5/2003 | Cronin et al. | |
| 6,579,472 B2 | 6/2003 | Chung et al. | |
| 6,673,236 B2 | 1/2004 | Stanciulescu et al. | |
| 6,846,406 B2 | 1/2005 | Canos et al. | |
| 6,969,500 B2 | 11/2005 | Bonath et al. | |
| 7,001,585 B2 | 2/2006 | Swanson | |
| 7,144,499 B2 | 12/2006 | Han et al. | |
| 7,153,414 B2 | 12/2006 | DeSouza | |
| 7,171,368 B1 | 1/2007 | Sisson et al. | |
| 7,314,545 B2 | 1/2008 | Karas et al. | |
| 7,371,318 B2 | 5/2008 | Corma Canos et al. | |
| 7,374,666 B2 | 5/2008 | Wachs | |
| 7,598,426 B2 | 10/2009 | Fang et al. | |
| 7,648,625 B2 | 1/2010 | Bhan et al. | |
| 7,678,264 B2 | 3/2010 | Bhan | |
| 7,749,374 B2 | 7/2010 | Bhan et al. | |
| 7,790,021 B2 | 9/2010 | Kocal et al. | |
| 7,875,185 B2 | 1/2011 | Zhang | |
| 7,918,992 B2 | 4/2011 | Bhan | |
| 7,919,992 B2 | 4/2011 | Rossi | |
| 8,088,706 B2 | 1/2012 | Domokos et al. | |
| 8,197,671 B2 | 6/2012 | Rankin et al. | |
| 8,241,490 B2 | 8/2012 | Litz et al. | |
| 8,298,404 B2 | 10/2012 | Litz et al. | |
| 8,372,777 B2 | 2/2013 | Bhan et al. | |
| 8,394,261 B2 | 3/2013 | Litz et al. | |
| 8,409,541 B2 | 4/2013 | Reynolds et al. | |
| 8,450,538 B2 | 5/2013 | Bhan et al. | |
| 8,450,540 B2 | 5/2013 | Van Den Berg et al. | |
| 8,481,450 B2 | 7/2013 | Bhan | |
| 8,492,599 B2 | 7/2013 | Bhan et al. | |
| 8,530,370 B2 | 9/2013 | Donaho et al. | |
| 8,562,817 B2 | 10/2013 | Milam et al. | |
| 8,562,818 B2 | 10/2013 | Milam et al. | |
| 8,597,608 B2 | 12/2013 | Reynolds et al. | |
| 8,608,946 B2 | 12/2013 | Bhan et al. | |
| 8,764,973 B2 | 7/2014 | Litz et al. | |
| 8,877,013 B2 | 11/2014 | Litz et al. | |
| 8,877,043 B2 | 11/2014 | Litz et al. | |
| 8,894,843 B2 | 11/2014 | Rankin et al. | |
| 8,961,779 B2 | 2/2015 | Litz et al. | |
| 9,061,273 B2 | 6/2015 | Litz et al. | |
| 9,206,359 B2 | 12/2015 | Litz et al. | |
| 2002/0177522 A1 | 11/2002 | Alexander, IV et al. | |
| 2002/0189975 A1 | 12/2002 | DeSouza | |
| 2003/0000867 A1 | 1/2003 | Reynolds | |
| 2003/0149317 A1 | 8/2003 | Rendina | |
| 2003/0170168 A1 | 9/2003 | Bonath et al. | |
| 2004/0108252 A1 | 6/2004 | DeSouza | |
| 2004/0178121 A1 | 9/2004 | Leyshon et al. | |
| 2004/0213730 A1 | 10/2004 | Swanson | |
| 2001/0222134 | 11/2004 | DeSouza | |
| 2004/0238410 A1 | 12/2004 | Inoue et al. | |
| 2005/0014850 A1 | 1/2005 | Hu | |
| 2005/0023188 A1 | 2/2005 | Connor | |
| 2006/0011510 A1 | 1/2006 | Toshima et al. | |
| 2006/0062722 A1 | 3/2006 | Liou | |
| 2006/0154814 A1 | 7/2006 | Zanibelli et al. | |
| 2006/0180501 A1 | 8/2006 | Da Silva et al. | |
| 2006/0231456 A1 | 10/2006 | Bhan | |
| 2006/0231457 A1 | 10/2006 | Bhan | |
| 2006/0234876 A1 | 10/2006 | Bhan | |
| 2007/0000810 A1 | 1/2007 | Bhan et al. | |
| 2007/0041890 A1 | 2/2007 | Brohan et al. | |
| 2007/0051667 A1 | 3/2007 | Martinie et al. | |
| 2007/0256980 A1 | 11/2007 | Krogue | |
| 2007/0295646 A1 | 12/2007 | Bhan et al. | |
| 2008/0083650 A1 | 4/2008 | Bhan et al. | |
| 2008/0087575 A1 | 4/2008 | Bhan et al. | |
| 2008/0121565 A1 | 5/2008 | Yoo et al. | |
| 2008/0135449 A1 | 6/2008 | Bhan et al. | |
| 2008/0308463 A1 | 12/2008 | Keckler et al. | |
| 2009/0065399 A1 | 3/2009 | Kocal et al. | |
| 2009/0188836 A1 | 7/2009 | Bhan et al. | |
| 2010/0055005 A1 | 3/2010 | Bhan et al. | |
| 2010/0098602 A1 | 4/2010 | Bhan et al. | |
| 2011/0000823 A1 | 1/2011 | Hamad et al. | |
| 2011/0011771 A1 | 1/2011 | Litz et al. | |
| 2011/0031164 A1 | 2/2011 | Litz et al. | |
| 2011/0108464 A1 | 5/2011 | Rankin et al. | |
| 2011/0178346 A1 | 7/2011 | Milam et al. | |
| 2011/0192762 A1 | 8/2011 | Wellington et al. | |
| 2011/0210043 A1 | 9/2011 | Wellington et al. | |
| 2011/0294657 A1 | 12/2011 | Soled et al. | |
| 2012/0055843 A1 | 3/2012 | Bourane et al. | |
| 2012/0055844 A1 | 3/2012 | Bourane et al. | |
| 2012/0055845 A1 | 3/2012 | Bourane et al. | |
| 2012/0055849 A1 | 3/2012 | Bourane et al. | |
| 2012/0067777 A1 | 3/2012 | Litz et al. | |
| 2012/0074040 A1 | 3/2012 | Koseoglu et al. | |
| 2012/0152804 A1 | 6/2012 | Koseoglu et al. | |
| 2012/0285864 A1 | 11/2012 | Rankin et al. | |
| 2012/0285866 A1 | 11/2012 | Litz et al. | |
| 2013/0015104 A1 | 1/2013 | Al-Hajji et al. | |
| 2013/0026062 A1 | 1/2013 | Al-Shahrani et al. | |
| 2013/0026071 A1 | 1/2013 | Koseoglu et al. | |
| 2013/0026075 A1 | 1/2013 | Koseoglu et al. | |
| 2013/0028822 A1 | 1/2013 | Bourane et al. | |
| 2013/0030236 A1 | 1/2013 | Koseoglu et al. | |
| 2013/0048543 A1 | 2/2013 | Litz et al. | |

(56) References Cited

U.S. PATENT DOCUMENTS

| | | | |
|---|---|---|---|
| 2013/0075305 | A1 | 3/2013 | Al-Shafei et al. |
| 2013/0130892 | A1 | 5/2013 | Litz |
| 2013/0171039 | A1 | 7/2013 | Graham et al. |
| 2013/0185044 | A1 | 7/2013 | Chen et al. |
| 2013/0315793 | A1 | 11/2013 | Koseoglu et al. |
| 2013/0334103 | A1 | 12/2013 | Bourane et al. |
| 2014/0024569 | A1 | 1/2014 | Bera et al. |
| 2014/0131256 | A1 | 5/2014 | Litz et al. |
| 2014/0291199 | A1 | 10/2014 | Litz et al. |
| 2014/0339136 | A1 | 11/2014 | Litz et al. |
| 2015/0337208 | A1 | 11/2015 | Litz et al. |

FOREIGN PATENT DOCUMENTS

| | | | |
|---|---|---|---|
| WO | WO 2006/093799 | A2 | 9/2006 |
| WO | 2008153633 | A1 | 12/2008 |
| WO | 2009120238 | A1 | 10/2009 |
| WO | 2012039910 | A1 | 3/2012 |
| WO | 2012051009 | A1 | 4/2012 |
| WO | 2013188144 | A1 | 12/2013 |
| WO | 2014018082 | A1 | 1/2014 |
| WO | 2014095813 | A1 | 6/2014 |

OTHER PUBLICATIONS

Jiang et al., "Hydrothermal synthesis of rutile TiO2 nanoparticles using hydroxyl and carboxyl group-containing organics as modifiers," Materials Chemistry and Physics, Aug. 1, 2006, 98(2-3):231-235.

Korean Office Action Translation for KR Appln. No. 2009-7024832.

Canadian Office Action for Appln. No. 2,719,058, mailed on Dec. 31, 2014.

Final Office Action (Mail Date May 6, 2016) for U.S. Appl. No. 12/598,474, filed Apr. 23, 2010.

El Nady, M. M. et al. (2013). Journal of Chemical and Engineering Data, 1, 1-7.

Dffice Action (Mail Date Apr. 22, 2016) for U.S. Appl. No. 14/286,342, filed May 23, 2014.

Energy Intelligence Group. (2007). "The Crude Oils and their Key Characteristics, " 7 pgs. (Available at http://www.energyintel.com/pages/eig_article.aspx?DocId=200017).

Office Action (Mail Date Jun. 15, 2016) for U.S. Appl. No. 14/246,508, filed Apr. 7, 2014.

European Office Action for Application No. 11 833 137.0-1361, mailed on Aug. 13, 2015.

Notice of Allowance for Canadian Appln No. 2,705,456, mailed on Sep. 17, 2015.

International Search Report and Written Opinion (mail date Feb. 16, 2016) for PCT Application No. PCT/US15/064587.

Notice of Allowance (Mail Date Aug. 4, 2015) for U.S. Appl. No. 14/287,916, filed May 27, 2014.

International Search Report and Written Opinion (mail date Aug. 4, 2015) for PCT Application No. PCT/US15/31461.

International Search Report and Written Opinion (mail date Aug. 5, 2015) for PCT Application No. PCT/US15/32417.

Jain, Suman L., et al. Rehenium-Catalyzed Highly Efficient Oxidations of Tertiary Nitrogen Compounds to N-Oxides Using Sodium Percarbonate as Oxygen Source. Synlett, 2006, No. 16, pp. 2661-2663. Published on Web Sep. 22, 2006 (Doc 1).

McKillop, Alexander, et al. Further Functional-Group Oxidations Using Sodium Perborate. Tetrahedron, vol. 45, No. 11, pp. 3299 to 3306, 1989. Published in Great Britain (Doc. 2).

Varma, Rajender S., et al. The Urea-Hydrogen Peroxide Complex: Solid-State Oxidative Protocols for Hydroxylated Aldehydes and Ketones (Dakin Reaction), Nitriles, Sulfides, and Nitrogen Heterocycles. Organic Letters, 1999, vol. 1, No. 2, pp. 189-191. Published on Web May 29, 1999 (Doc. 3).

Jana, Nirmal K., et al. Phase-Vanishing Methodology for Efficient Bromination, Alkylation, Epoxidation, and Oxidation Reactions of Organic Substrates. Organic Letters, 2003, vol. 5, No. 21, pp. 3787-3790. Published on Web Sep. 16, 2003 (Doc. 4).

Khodaei, Mohammad Mehdi, et al. H2O2/Tf2O System: An Efficient Oxidizing Reagent for Selective Oxidation of Sulfanes. Synthesis, 2008; No. 11, pp. 1682-1684. Published on Web Apr. 11, 2008 (Doc. 5).

Kim, Sung Soo, et al. A Mild and Highly Efficient Oxidation of Sulfide to Sulfoxides with Periodic Acid Catalyzed by FeCl3. Synthesis, 2002, No. 17, pp. 2484-2486. Published USA Feb. 12, 2002 (Doc. 6).

Qian, Weixing, et al. Efficient and Highly Selective Oxidation of Sulfides to Sulfoxides in the Presence of an Ionic Liquid Containing Hypervalent Iodine. Synlett, 2006, No. 5, pp. 709-712. Published on Web Mar. 9, 2006 (Doc. 7).

Matteucci, Mizio, et al. Mild and Highly Chemoselective Oxidation of Thioethers Mediated by Sc(OTf)3. Organic Letters, 2003, vol. 5, No. 3, 235-237. Published on Web Jan. 11, 2003 (Doc. 8).

Mba, Myriam, et al. C3-Symmetric Ti(IV) Triphenolate Amino Complexes as Sulfoxidation Catalysts with Aqueous Hydrogen Peroxide. Organic Letters, 2007, vol. 9, No. 1, pp. 21-24. Published on Web Dec. 9, 2006 (Doc. 9).

Drago, Carmelo, et al. Vanadium-Catalyzed Sulfur Oxidation/Kinetic Resolution in the Synthesis of Enantiomerically Pure Alkyl Aryl Sulfoxides. Agnew. Chem. Int. Ed, 2005, 44, pp. 7221-7223. Published on Web Oct. 17, 2005 (Doc. 10).

Egami, Hiromichi, et al. Fe(salan)-Catalyzed Asymmetric Oxidation of Sulfides with Hydrogen Peroxide in Water. J. Am. Chem. Soc., 2007, vol. 129, No. 29, pp. 8940-8941. Published on Web Jun. 29, 2007 (Doc. 11).

Sun, Jiangtao, et al. Efficient Asymmetric Oxidation of Sulfides and Kinetic Resolution of Sulfoxides Catalyzed by a Vanadium-Salan System. J. Org. Chem., 2004, vol. 69, No. 24, pp. 8500-8503. Published on Web Oct. 28, 2004 (Doc. 12).

Karimi, Babak, et al. Selective Oxidation of Sulfides to Sulfoxides Using 30% Hydrogen Peroxide Catalyzed with a Recoverable Silica-Based Tungstate Interphase Catalyst. Organic Letters, 2005, vol. 7, No. 4, pp. 625-628. Published on Web Jan. 25, 2005 (Doc. 13).

Ali, Mohammed Hashmat, et al. Ceric Ammonium Nitrate Catalyzed Oxidation of Sulfides to Sulfoxides. Synthesis, 2007, No. 22, pp. 3507-3511. Published on Web Oct. 16, 2007 (Doc. 14).

Imada, Yasushi, et al. Flavin Catalyzed Oxidations of Sulfides and Amines with Molecular Oxygen. J. Am Chem. Soc., 2003, vol. 125, No. 10, pp. 2868-2869. Published on Web Feb. 12, 2003 (Doc 15).

Varma, Rajender S., et al. The Urea-Hydrogen Peroxide Complex: Solid-State Oxidatives Protocols for Hydroxylated Aldehydes and Ketones (Dakin Reaction), Nitriles, Sulfides, and Nitrogen Heterocycles. Organic Letters, 1999, vol. 1, No. 2, pp. 189-191. Published on Web May 29, 1999 (Doc. 16).

Jana, Nirmal K.,e t al. Phase-Vanishing Methodology for Efficient Bromination, Alkylation, Epoxidation, and Oxidation Reactions of Organic Substrates. Organic Letters, 2003, vol. 5, No. 21, pp. 3787-3790. Published on Web Sep. 16, 2003 (Doc. 17).

Shaabani, Ahmad, et al. Green oxidations. The use of potassium permanganate supported on manganese dioxide. Tetrahedron, 2004, 60, pp. 11415-11420. Published on Web Oct. 12, 2004 (Doc. 18).

Wozniak, Lucyna A., et al. Oxidation in Organophosphorus Chemistry: Potassium Peroxymonosulphate. Tetrahedron, 1999, 40, pp. 2637-2640. Received Oct. 13, 1998; Accepted Feb. 3, 1999. No published date. (Doc. 19).

Akasaka, Takeshi,e t al. Singlet Oxygen Oxidation of Organophosphorus Compounds: Cooxidation of Olefin with Phosphadioxirane. Quimica Nova, 1993, 16, pp. 325-327. No published date or location (Doc. 20).

Milner, O.I., et al. Determination of Trace Materials in Crudes and Other Petroleum Oils. Analytical Chemistry, vol. 24, No. 11. Published Nov. 1952, USA (Doc. 21).

Aida, Tetsuo, et al. Development of an Efficient Coal-Desulfurization process: "Oxy-Alkalinolysis". Technical Report Resource Conference: American Chemical Society symposium on coal liquefaction, pp. 328-334. Kansas City, MO USA. Published Sep. 1, 1982

(56) References Cited

OTHER PUBLICATIONS

Ames Lab., IA (USA); Advanced Fuel Research, Inc., East Hartford, CT (USA) (Doc. 22).

Aida, Tetsuo, et al. Reaction of Dibenzothiophene Sulfone with Alkoxides. Tetrahedron Letters (1983), vol. 24, No. 34, pp. 3543-3546. USA (Doc. 23).

Oviedo, Alberto, et al. Deoxydesulfurization of sulfones derived from dibenzothiophene using nickel compounds. Journal of Molecular Catalysis A: Chemical, (2008) 293, pp. 65-71. USA (Doc. 24).

Ripin, D.H., et al., "pKa's of Inorganic and Oxo-Acids", [http://evans.harvard.edu/pdf/evans_pka_table.pdf]; published Apr. 11, 2005, accessed Apr. 29, 2013. 6 pages.

Application No. PCT/US2008/82095, International Search Report and the Written Opinion of the International Searching Authority, or the Declaration dated Mar. 20, 2009. 12 pages.

Application No. PCT/US2011/50159, International Search Report and the Written Opinion of the International Searching Authority dated Jan. 12, 2012, 11 pages.

Application No. PCT/US2011/54840, International Search Report and the Written Opinion of the International Searching Authority dated Mar. 12, 2012, 8 pages.

Application No. PCT/US2011/70243, Internatinoal Search Report and the Written Opinion of the International Searching Authority dated Feb. 25, 2013, 40 pages.

Application No. PCT/US2013/43843, International Search Report and the Written Opinion of the International Searching Authority dated Aug. 27, 2013, 7 pages.

Office Action (Mail Date Jan. 21, 2015) for U.S. Appl. No. 14/287,916, filed May 27, 2014.

Office Action (Mail Date Jun. 19, 2015) for Patent Application No. 14/287,916 - Filing Date May 27, 2014; Attorney Docket No. AUTE6964CIPCIP2-Ny.

* cited by examiner

PRODUCT CONTAINING MONOMER AND POLYMERS OF TITANYLS AND METHODS FOR MAKING SAME

CROSS-REFERENCE TO RELATED APPLICATIONS

This application is the U.S. National Phase of PCT/US2008/005624, filed May 2, 2008, which claims priority to U.S. Provisional Application No. 60/924,214, filed on May 3, 2007; 60/917,171, filed on May 10, 2007; and 61/039,619 filed on Mar. 26, 2008, the entire contents of which are incorporated herein by reference for any and all purposes.

FIELD

The present invention relates generally to the field of nanoparticulate materials and methods of their preparation. More specifically, the present invention relates to metal oxy alkoxide materials that may be precursors to nanoparticulate materials.

BACKGROUND

Titanium dioxide ($TiO_2$) is a ubiquitous white pigment used in the paint and coatings industry, and is also prevalent in the semiconductor industry. $TiO_2$ exists both naturally and synthetically in three forms: rutile, anatase, and brookite. Synthetic methods to prepare $TiO_2$ typically involve variants of hydrolysis of titanium tetrachloride ($TiCl_4$) or titanium oxychloride (titanyl chloride). For example, it has been known for over 100 years that reacting $TiCl_4$ with water results in $TiO_2$ by the following reaction (see B. J. Harrington, Trans. Royal Soc. (Canada), [2], 1, 3 (1895)):

$$TiCl_4 + 2H_2O \rightarrow TiO_2 + 4HCl$$

As is readily observed, HCl is a by-product of such hydrolyses. Such an acidic environment can also be problematic in many applications. For example, such an acidic environment can break down the binders and other additives to materials having incorporated $TiO_2$, or react with substrates to which a $TiO_2$-containing coating or material is applied. It should also be noted that $TiCl_4$ is a hazardous material, mainly due to the acid-byproducts caused by rapid hydrolysis, and it requires special handling precautions.

As noted in the Encyclopedia of Chemical Reactions, vol. 7, page 404 "[r]utile crystals are obtained by the action of water vapor upon volatile titanium chloride." The above reaction has been used by the $TiO_2$ producing industries to produce bulk $TiO_2$ powders in large quantities. As used herein, bulk powder means a powder having an average particle size of greater than 100 nm, such as 1 micron or greater.

For a wide range of commercial applications, materials with one or more of the following properties are desirable: (a) the ability to form nanoparticles which can be dispersed in both water as well as organic solvents, (b) a high optical transparency in the visible range (400-700 nm) and high UV absorption (wavelength below 400 nm), (c) maintaining the optical properties described in (b) above, while increasing particle loading density in other materials beyond just a few weight percentage, such as beyond 5-10 weight percent, and (d) absence of a shell of different material on the nanoparticles to allow the nanoparticles to link or chemically bond with solid matrix materials, such as polymers. Early transition metal-based sol gels (i.e. sols), such as those of Ti, Zr, or Hf, may exhibit such desirable properties.

Hence, preparation of titanium and zirconium sols are desired in which residual acid and metal oxide formation due to hydrolysis is minimized and the optical and electrical properties of the materials are preserved.

SUMMARY

In one aspect, a composition is provided of a compound of formula I: $M_mO_m(OR^2)_n$ (I), or a mixture of any two or more thereof. In one embodiment, M is Ti, Zr, or Hf; $R^2$ at each occurrence is individually a substituted alkyl group containing at least one OH group, a substituted cycloalkyl group containing at least one OH group, a substituted cycloalkylalkyl group containing at least one OH group, a substituted heterocyclyl group containing at least one OH group, or a heterocyclylalkyl containing at least one OH group; and m and n are independently an integer from one to eight. In some embodiments, the compound of formula I is a compound of formula II, or III:

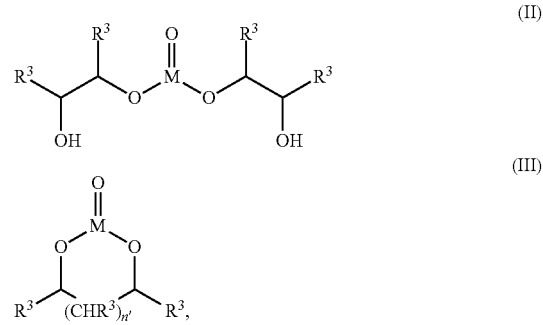

an isomer of the compound of Formula II or III, or a mixture of any two or more compounds and/or isomers. In such embodiments, M is Ti or Zr; $R^3$ at each occurrence is independently H, F, Cl, Br, I, CN, $OR^4$, $NR^5R^6$, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; $R^4$ is H, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; $R^5$ and $R^6$ are independently H, substituted or unsubstituted alkyl, substituted or unsubstituted cycloalkyl, substituted or unsubstituted heterocyclylalkyl, or $R^5$ and $R^6$ may join to form a heterocyclic ring containing the N to which they are attached; and n' is 0, 1, 2, 3, or 4.

In some embodiments of the compound, M is Ti. In some other embodiments of the compound, $R^3$ at each occurrence is independently H, $OR^4$, or a substituted or unsubstituted alkyl group. In other embodiments, the compound is bis(ethylene glycol)oxotitanium (IV), bis(glycerol)oxotitanium (IV), bis(erythritol)oxotitanium (IV), or bis(sorbitol)oxotitanium (IV). Such compounds described above may have a visible wavelength range transmittance of at least 90% and/or an ultra-violet light transmittance of less than about 20% in a wavelength range below about 400 nm.

In another aspect, a process is provided including reacting a compound of formula $MOX_2$ with a reagent comprising at least one hydroxyl groups to form a first reaction mixture including the compound described above, HX, water, and the reagent; where the reagent is selected from alcohols, polyols, sugars, or starches; and X is a halide selected from the group consisting of F, Cl, Br, and I. Such processes may also include removing HX by at least one of evaporation or neutralization to form a second reaction mixture. Reagents may include, but are not limited to polyols such as ethylene glycol, glycerol, erythritol, and sorbitol. In some embodiments, the HX is removed by reacting a base with the first reaction mixture. Exemplary bases may include alkali metal alkoxides, alkaline earth alkoxides, primary amines, secondary amines, and tertiary amines, such as but not limited to triethylamine, diisopropyl amine, trimethyl amine, tripropyl amine, tributylamine, or tert-butyl-methylamine.

In other aspects, compositions including one or more of the above compounds and a solvent, or one or more of the above compounds in a polymeric resin, are also provided. Such solvents may include polar organic solvents and water. Such polymeric resins may include polyurethanes; polyethylene glycol; epoxy resins; polyacrylates; polyamides; polyesters; polyacrylonitriles; cellulosics including, but not limited to acetates, nitrates, and the like; phenolic resins; pentaerythritol resins; polyvinylpyrrolidone; polysaccharides; polyglucuronates; co-polymers of such materials, or blends of any two or more. In some embodiments of the compound in a polymeric resin, the compound of Formula II, III, or the mixture of any two or more causes a change in the refractive index of the resin as compared to a neat resin. In such embodiments, the neat resin is the resin without any of the identified compounds added. In other embodiments, the compound of formula I, II, or III, or the mixture of any two or more are hydrolyzed and cause a change in the refractive index of the resin as compared to a neat resin.

In another aspect, devices incorporating such compositions are provided. In other aspects, a device is provided having a thin film of the compound of formula $M_mO_m(OR^2)_n$ on a substrate.

In another aspect, method of adjusting the refractive index of a polymer are provided, including doping the polymer with one or more of the above compounds of formula $M_mO_m(OR^2)_n$. The polymer may be doped at a level from about 1% to about 90%.

In another aspect, methods of preparing a particle by hydrolyzing a compound of formula $M_mO_m(OR^2)_n$ to form a hydrosylate are provided. In such an aspect, the hydrosylate may include a polyoxotitanate. The particle may also be a nanoparticle. Such nanoparticles may then be doped into a polymer at a level from about 1% to about 90%, and this may result in an adjustment in the refractive index of the polymer. In some embodiments, a plurality of the particles have a visible transmittance of 90%, and in other embodiments, the plurality of the particles has an ultra-violet light transmittance of less than about 20% below 400 nm. Compositions of a plurality of the nanoparticles formed by such methods are also provided.

In other embodiments, the hydrosylate may be calcined to form titania or zirconia.

In another aspect, a coating solution is provided, including a composition of nanoparticles dispersed in a first liquid and a second liquid; where, the first liquid has a vapor pressure; the second liquid has a vapor pressure that is less than the vapor pressure of the first liquid; the first and second liquids are miscible; and the nanoparticles are more compatible with the first liquid. In some embodiments, the second liquid is a curable liquid. Such second liquids may include acrylates, methacrylates, epoxies, polyesters, polyols, isocyanates, polystyrene, polyacrylates, polymethacrylates, polyurethanes, or a mixture of any two or more. Exemplary acrylates include isooctyl acrylate, 2-ethylhexyl acrylate, 1,6-hexanediol diacrylate, or a mixture of any two or more. In other embodiments, the second liquid is water, an organic solvent, an inorganic solvent, or a mixture of any two or more such liquids. In some embodiments, the coating solution may also include a cross-linker. The first liquid may be water, an organic solvent, an inorganic solvent, or a mixture of any two or more. Exemplary organic solvents include alcohols, ketones, aromatic hydrocarbons, and a mixture of any two or more thereof.

In some embodiments, the coating solution may also contain materials such as dyes, pigments, fillers, electrically conductive particles, thermally conductive particles, fibers, film-forming polymers, catalysts, initiators, or a mixture of any two or more such materials. Such film-forming polymers may be adhesives, polyacrylates, polyurethanes, epoxies, silicones, polyethylene oxides, copolymers thereof, block polymers thereof, or a mixture of any two or more such materials. For example, polyacrylates may include polymethylmethacrylate, co-polymers of polymethylmethacrylate, polyhydroxyethylmethacrylate, co-polymers of polyhydroxyethylmethacrylate, or a mixture of any two or more such acrylates.

In another aspect an encapsulated solid state device is provided. Such encapsulated devices may include a solid state device and an encapsulant; where the encapsulant includes (A) greater than about 40 wt % of a silicone epoxy resin; (B) between about 1 wt % and about 20 wt % of the hydrosylate prepared by hydrolyzing a compound of formula $M_mO_m(OR^2)_n$; (C) less than about 25 wt % of an anhydride curing agent; and (D) between about 0.008 wt % and about 10 wt % of an ancillary curing catalyst; where the wt % amounts are based on the combined weight of (A), (B), (C) and (D). In some embodiments, the solid state device is a semiconductor device. In other embodiments, the solid state device is an opto-electronic device. In further embodiments, the opto-electronic device is an integrated circuit, a LED, a CCD, a memory or logic device, a photodiode, a phototransistor, or an opto-electronic coupler. In some embodiments, the encapsulant may also include an additive such as thermal stabilizers, UV stabilizers, cure modifiers, coupling agents, refractive index modifiers, or a mixture of any two or more such materials.

In some embodiments, the silicone epoxy resin includes a silicon moiety selected from $R_3SiO_{0.5}$, $R_2SiO$, $RSiO_{1.5}$, or $SiO_2$; and an epoxy-containing silicone moiety selected from $EpR_2SiO_{0.5}$, $EpRSiO$, or $EpSiO_{1.5}$; where Ep is an epoxy moiety selected from glycidoxypropyl, 3,4-epoxycyclohexane ethyl, or 1,2-epoxy hexyl; and R is selected from hydrogen, alkyl, halogen-substituted alkyl, or aryl. For example the silicone epoxy resin includes 1,1,3,3-tetramethyl-1,3-bis[2(7-oxabicyclo[4.1.0]hept-3-yl)ethyl]disiloxane.

In some embodiments, the anhydride curing agent includes bicyclo[2.2.1]hept-5-ene-2,3-dicarboxylic anhydride, methylbicyclo[2.2.1]hept-5-ene-2,3-dicarboxylic anhydride, bicyclo[2.2.1]hept-5-ene-2,3-dicarboxylic anhydride, phthalic anhydride, pyromellitic di-anhydride, hexahydrophthalic anhydride, hexahydro-4-methylphthalic anhydride, dodecenylsuccinic anhydride, dichloromaleic anhydride, chlorendic anhydride, tetrachlorophthalic anhydride, or a mixture of any two or more such anhydrides. In such embodiments, the anhydride curing agent may be hexahydro-4-methylphthalic anhydride.

In other aspects, the compound of formula $M_mO_m(OR^2)_n$ may be used as an esterification catalyst, a transesterification catalyst, or a crosslinker.

In other aspects, multi-component ultraviolet stabilizer systems for coatings are provided. Such systems include a composition of the compound of formula $M_mO_m(OR^2)_n$ or a hydrosylate of the compound; a substituted hydroxyphenylbenzotriazole, and a hindered amine light stabilizer.

In another aspect, the compound of formula I may be used in a method of decontaminating a fuel. In some embodiments, the method includes providing a fuel comprising a fuel source, preparing a mixture of the fuel, a compound of formula I, an organic acid; and an oxidant; and recovering a decontaminated fuel. In some embodiments, the compound of formula I is selected from the group consisting of bis(ethyleneglycol)oxotitanium (IV), bis(glycerol)oxotitanium (IV), bis(erythritol)oxotitanium (IV), or bis(sorbitol)oxotitanium (IV). In other embodiments, the organic acid is selected from the group consisting of $HCO_2H$, $CH_{3-x}Cl_xCO_2H$, $CF_3CO_2H$, and mixtures of any two or more thereof, wherein x is an integer from 0-3. In yet other embodiments, the oxidant is selected from the group consisting of nitrogen oxides, nitric acid, hydrogen peroxide, ozone, organic peroxides, oxygen, air, peracids, and mixtures of any two or more thereof.

Another embodiment relates to a sulfoxidation method, comprising: providing a hydrocarbon solution, said solution comprising a sulfur compound; providing a catalytic solution, said catalytic solution comprising a metal alkoxide represented by the formula $M_mO_m(OR)_n$; and contacting said hydrocarbon solution with said catalytic solution in the presence of an oxidant, resulting in said oxidant oxidizing said sulfur compound.

Another embodiment relates to a catalytic sulfoxidation reagent, comprising: an acidic solvent; a metal alkoxide represented by the formula $M_mO_m(OR)_n$ dissolved in said solvent; and an oxidant dissolved in said solvent.

Another embodiment relates to a sulfoxidation method, comprising; introducing a hydrocarbon solution into a reaction vessel, said hydrocarbon solution comprising a sulfur compound; and introducing a catalyst solution into said vessel, resulting in said catalyst solution contacting said hydrocarbon solution, said catalyst solution comprising a metal alkoxide catalyst represented by the formula $M_mO_m(OR)_n$, resulting in forming a mixture, resulting in said catalyst catalyzing an oxidation reaction between said oxidant and said sulfur compound and oxidizing said sulfur compound. resulting in said oxidized sulfur compound having a higher solubility in said catalyst solution than in said hydrocarbon solution.

DETAILED DESCRIPTION

Figure 1:
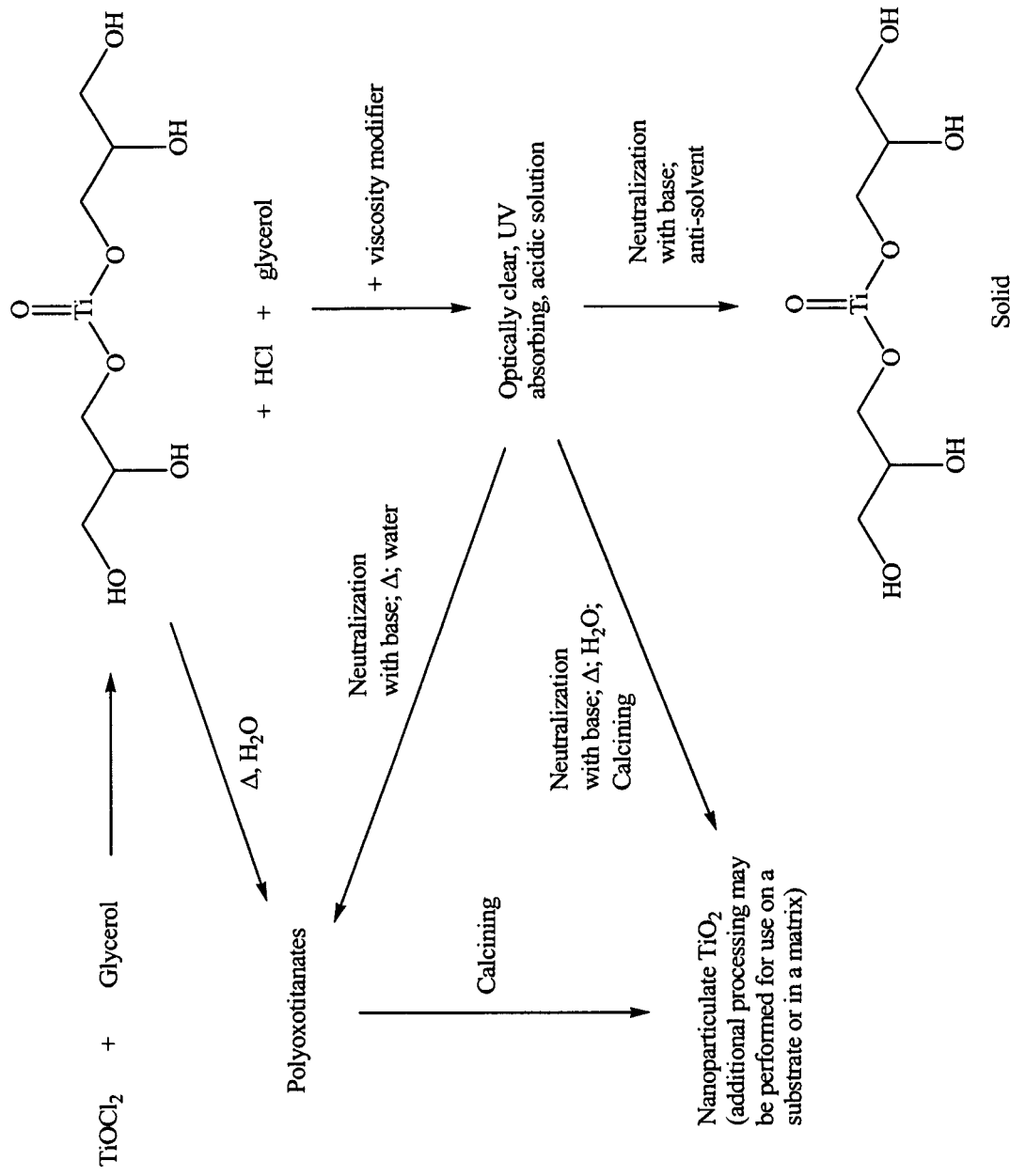
FIG. 1 is a scheme (Scheme I) showing compounds and methods of preparation according to one or more embodiments of the invention. Titanyl compounds are exemplified in the scheme.

Compositions of matter and processes of preparing compounds of the formula $M_mO_m(OR^1)_n$ are provided, where M is Ti or Zr, $OR^1$ is derived from a regent containing at least two OH groups and m and n are 1-8. For example, the reagent may be a polyol or an alcohol such as, but not limited to, ethylene glycol, glycerol, diethyleneglycol monomethylether, diethyleneglycol monobutylether, erythritol, or sorbitol, and the like; a sugar; or a starch. In some embodiments, where m equals n, $R^1$ forms a ring structure with the titanium atom forming a ring containing at least five members. As part of the synthetic process, residual acid is removed and/or neutralized from the reaction solution. The resulting compositions of matter are useful as precursors to $TiO_2$ in that they don't produce HCl as the by-product of hydrolysis, but rather simple alcohols. This makes them much more suited as additives to plastics, solvents, coatings, and the like where titanium oxychloride would be unsuitable. The reaction products are distinguished from typical alkoxytitanates in that those embodied herein appear to maintain the Ti=O bond. This bond appears to be important in maintaining strong UVC-UVB absorption as compared to tetralkoxytitanates. Furthermore, the compounds embodied herein permit formulation of UV-absorptive, visibly transparent titanium materials without the milky white color afforded by traditional titania and zirconia nanoparticles.

DEFINITIONS

For the purposes of this disclosure and unless otherwise specified, "a" or "an" means "one or more."

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In general, "substituted" refers to an alkyl, cycloalkyl, cycloalkylalkyl, heterocyclyl, or heterocyclylalkyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, heterocyclyloxy, and heterocyclylalkoxy groups; carbonyls (oxo); carboxyls; esters; ethers; urethanes; alkoxyamines; thiols; sulfides; sulfoxides; sulfones; sulfonyls; sulfonamides; amines; N-oxides; isocyanates; cyanates; thiocyanates; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with substituted or unsubstituted alkyl or alkenyl groups as defined below.

Alkyl groups include straight chain and branched alkyl groups having from 1 to 12 carbon atoms or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups can be substituted at the alkyl, the cycloalkyl or both the alkyl and cycloalkyl portions of the group. Representative substituted cycloalkylalkyl groups can be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups can be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups can be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. However, the phrase "heterocyclyl group" does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydropyranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl(azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups can be substituted at the alkyl, the heterocyclyl or both the alkyl and heterocyclyl portions of the group. Representative heterocyclyl alkyl groups include, but are not limited to, 4-ethylmorpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups can be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups can be substituted one or more times with substituents such as those listed above.

As used herein, the phrase "high boiling point" includes materials having a boiling point in excess of 50° C., 60° C., 70° C., 80° C., 90° C., 100° C., 120° C., 140° C., 160° C., 180° C., or 200° C. at atmospheric pressure. In some embodiments, a high boiling point material has a boiling point from about 200° C. to about 600° C. at atmospheric pressure.

The term "amine" (or "amino") as used herein refers to —NR$^5$R$^6$ groups, wherein R$^5$ and R$^6$ are independently H, substituted or unsubstituted alkyl, substituted or unsubstituted cycloalkyl, substituted or unsubstituted heterocyclylalkyl, or R$^5$ and R$^6$ may join to form a heterocyclic ring and/or group containing the N to which they are attached. In some embodiments, the amine is NH$_2$, methylamino, dimethylamino, ethylamino, diethylamino, propylamino, dipropylamino, isopropylamino, diisopropylamino, phenylamino, or benzylamino.

The term "nanoparticles" includes particles having an average size between about 2 and about 100 nm, in some embodiments, or an average size between about 2 and about 50 nm, in other embodiments. The nanoparticles may also have an average size of between about 2 and about 10 nm. The first standard deviation of the size distribution may be 60% or less, 40% or less, or from 10 to 25% of the average particle size, each in various embodiments. The nanoparticles may also include oxide nanoparticles, such as metal or semiconductor oxide nanoparticles, such as titanium oxide, or zirconium oxide. Specifically, the nanoparticles may comprise titania, zirconia, or hafnium oxide nanoparticles, which in their pure, stoichiometric state can be expressed by the following respective chemical formulas: TiO$_2$, ZrO$_2$ and HfO$_2$.

As used herein, the term "reactive distillation" is a process where the chemical reactor is also the still. Separation of a material from the reaction mixture does not need a separate distillation step, which saves energy (for heating) and materials.

As used herein, the term "reactive extrusion" is a process where the chemical reactor is the extruder. Separation of a material from the reaction mixture occurs during the extrusion process, so the end product exits the extruder.

Compounds

In one aspect, a compound of formula $M_mO_m(OR^2)_n$, or a mixture of any two or more is provided, where M is Ti, Zr, or Hf; R$^2$ at each occurrence is a substituted alkyl group containing at least one OH group, a substituted cycloalkyl group containing at least one OH group, a substituted cycloalkylalkyl group containing at least one OH group, a substituted heterocyclyl group containing at least one OH group, or a heterocyclylalkyl containing at least one OH group; and m and n are independently 1-8. For example, R$^2$ may be derived from a polyol, a sugar, or a starch. Suitable polyols include, but are not limited to ethylene glycol, propyleneglycol, glycerol, erythritol, ethylene glycol butyl ether, and sorbitol. In some embodiments, m is one and n is two. In some cases, the compositions may have two or more different compounds of formula $M_mO_m(OR^2)_n$. In some embodiments, the compound has the Formula (I):

(I)

In some embodiments, the compound of formula $M_mO_m(OR^2)_n$, has the formula $M_mO_m(OCHR^3CH(OH)R^3)_n$ (II), or a mixture of any two or more. In such compounds, M is typically selected from an early transition metal such as Ti, Zr, or Hf. At each occurrence, R$^3$ may be independently selected from, but not limited to, H, F, Cl, Br, I, CN, OR$^4$, NR$^5$R$^6$, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; R$^4$ is selected from, but is not limited to, H, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl; R$^5$ and R$^6$ are independently H, substituted or unsubstituted alkyl, substituted or unsubstituted cycloalkyl, substituted or unsubstituted heterocyclylalkyl, or R$^5$ and R$^6$ may join to form a heterocyclic ring containing the N to which they are attached; m is typically and integer from 1 to 8; and n is typically an integer from 1 to 8. The compound of Formula II thus described, may be represented by the following formula, where m is one and n is two:

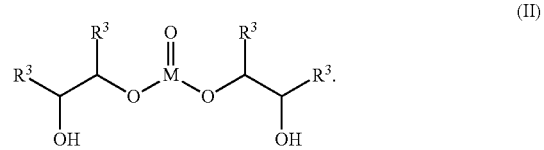

(II)

In other embodiments, the compound of formula $M_mO_m(OR^2)_n$ is provided where n is equal to m, and the 0 oxygen of the at least one OH group on R$^2$ is deprotonated and is attached to M, thus forming a ring structure having five or more ring members. Such ring structures may be represented by the Formula (III):

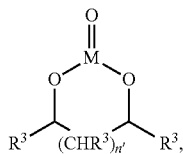

(III)

where n' is 0, 1, 2, 3, or 4.

In some embodiments, the compound of Formula I is a titanyl compound. Examples of such titanyl compounds include bis(ethyleneglycol)oxotitanium (IV), bis(glycerol)oxotitanium (IV), bis(erythritol)oxotitanium (N), and bis(sorbitol)oxotitanium (IV), but the scope of the titanyl compounds embodied herein is not so limited.

Where polyols, or other reagents having multiple —OH groups, are used to prepare the compounds embodied herein, multiple —OH groups on the reagent are available for bonding to the metal atom. This can result in a number of possible regioisomers of the compounds prepared. As a non-limiting example, where the compound is bis(glycerol)oxotitanium (IV), the compound may be represented by the following formulas:

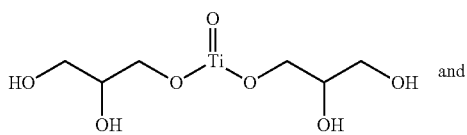 and

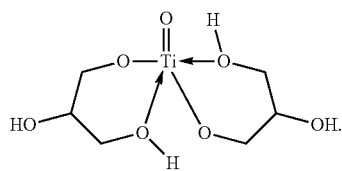

At least two other regioisomers exist. Such isomers are known to those of skill in the art and may include any of the —OH groups on the glycerol moiety attached to the metal. One such regioisomer is:

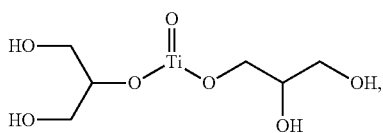

and another such regioisomer is:

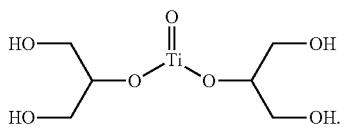

Because, the glycerol moiety contains a chiral center in the instances where the compound has a Ti—O—CH$_2$C*H(OH)CH$_2$(OH) fragment, with * indicating the chiral center, at least six stereoisomers of the above regioisomers are also known and will be readily recognized by those of skill in the art.

As a non-limiting example, where the compound is bis(ethyleneglycol)oxotitanium, the compound may be represented by the following formula:

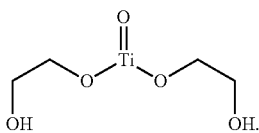

In one embodiment, the compound has the following properties: a visible transmittance of 90%, an ultra-violet light transmittance of less than about 20% below 400 nm, optical clarity, and/or optically and spectroscopically colorless. Transmission and absorbance are based upon a 10% w/w solution as measured in a one cm quartz cell.

In some embodiments, the compounds are susceptible to hydrolysis to form organometallic polymers, such as polyoxometallates or other materials that result from an incomplete hydrolysis of the compounds such that some polyol functionality remains on the periphery of the hydrolyzed product. Polyoxometallates may include materials such as, but not limited to polyoxotitanates or polyoxozirconates that have alcohol or polyol functionality.

In some other embodiments, the hydrolysis products may be calcined to form nanoparticles of the corresponding metal dioxide, such as titanium dioxide (i.e. titania), zirconium dioxide (i.e. zirconia), or hafnium dioxide. For example, the compound of Formula II, where M is Ti, may be hydrolyzed in the presence of heat to form TiO$_2$ nanoparticles.

In another aspect, a process for preparing compounds of Formulas I, II, and III, is provided. As shown in FIG. 1, In some embodiments, the first step in the process involves reacting a compound of formula MOX$_2$ with a reagent having at least one hydroxyl group to form a first reaction mixture that includes the compound of Formula I, II, and/or III and HX. The first reaction mixture may also contain water, and polyol. Optionally, a viscosity modifier, such as methoxypropanol, may be added to the first reaction mixture. Also as depicted in FIG. 1, the HX may then be removed by evaporation, such as through simple evaporation, reactive distillation, or reactive extrusion; and/or through neutralization to form a second reaction mixture, containing the compound of Formula I, II, and/or III, water, and polyol. As referred to above, M is a metal selected from Ti, Zr, and Hf; and X is a halogen atom such as F, Cl, Br, or I. Reagents that are suitable for use in the process include, but are not limited to, polyols, alcohols, sugars, and starches having a high boiling point. The first reaction mixture may be an optically clear, UV absorbing, acidic material may then be neutralized by reaction with a base to form the second reaction mixture. The resulting solution may then be further modified by a number of other processes.

As noted above, the HX may be removed through reactive distillation or reactive extrusion in some cases. In such processes the hydrolysis is carried out either in the reactor or in the extruder, and HX is remove from the reaction mixture. In the case of reactive distillation, HX may be removed as a gas from the reactor. In the case of reactive extrusion, HX may be removed from the extruder via vent ports located in the extruder. Without being bound by theory, it is believed that removal of the HX from the reaction mixture, drives the hydrolysis reaction to completion.

In some embodiments, the compound of formula MOX$_2$ is present at a concentration of from about 20% to about 50%, from about 25% to about 45%, from about 30% to about 40%, or from about 35% to about 36% prior to reaction with the organic reagent. In other embodiments, reagent is added at an amount of two equivalents per every equivalent of the compound of formula $MOX_2$.

In some embodiments, the polyol is a substituted alkyl group, a substituted cycloalkyl group, a substituted cycloalkylalkyl group, a substituted heterocyclyl group, or a substituted heterocyclylalkyl group, having two or more OH groups which are capable of reacting with the $MOX_2$ compound. Suitable polyols include, but are not limited to, ethylene glycol, glycerol, propylene glycol, butanediols, butanetriols, erythritol, and sorbitol.

The step of removing HX by neutralization involves reacting the compound with a base to remove the HX. Suitable bases include OH-free bases such as, but are not limited to, alkali metal alkoxides, alkaline earth alkoxides, and amines, including, but not limited to, primary amines, secondary amines, tertiary amines, and heterocyclylalkylamines. Suitable amines may be selected from, but are not limited to, triethylamine, diisopropyl amine, trimethyl amine, tripropyl amine, tributylamine, and tert-butyl-methylamine. The HX that is generated by the compound formation reaction reacts with the base to form a salt that may be removed from the reaction mixture in some embodiments. In the instance where the base is selected from alkali metal alkoxides, and alkaline earth alkoxides, the result is the formation of a salt of X and the alkali metal or alkaline earth metal. In the instance where the base is selected from an amine, the result is an ammonium salt of X. In either instance, the salt of X is then removed from the reaction mixture by decantation, centrifugation followed by decantation, cannulation, filtration, or sublimation.

As a non-limiting example, titanium compounds may be formed, as shown in FIG. 1. For example, the $TiOCl_2$ may be reacted with glycerol, a high boiling polyol, and after the first step of the process, i.e. formation of the first reaction mixture, an optically clear, UV absorbing, acidic material is formed containing $TiO(OCH_2CH(OH)CH_2OH)_2$, or an isomer, HCl, glycerol, and optionally water. In some embodiments, the pH of the solution is less than one.

As discussed above, the second reaction mixture, i.e. the base neutralization product, may be used in a number of other processes. In some embodiments, the process includes precipitating a compound of Formula I, II, or III from the filtrate. In some embodiments, this precipitation is effected by the addition of an anti-solvent, as shown in FIG. 1. Such anti-solvents may be any one of a number of non-polar solvents, or a mixture of any two or more solvents. For example, anti-solvents may include, but are not limited to acetone, alkanes such as pentane, hexane, or octane, benzene, toluene, tetrahydrofuran, diethyl ether, methyl-2-pentanone, methyl tert-butyl ether, methyl ethyl ketone, and/or mixtures of any two or more anti-solvents.

Compositions/Devices

Compositions containing the compounds of Formula I, II, III, or mixtures of any two or more of those compounds in a solvent are also provided. The solvent may be a viscosity modifier. Suitable solvents and viscosity modifiers for such compositions include, but are not limited to polar organic solvents and water. For example, suitable polar organic solvents may include methanol, ethanol, propanol, butanol, tert-butanol, methoxypropanol, trimethoxy propanol, propylene glycol, ethylene glycol, glycerol, DMSO, DMF, pyridine, and/or a mixture of any two or more such solvents.

Other compositions may include the compounds of Formulas I, II, III or a mixture of any two or more, and a polymeric resin. Suitable polymeric resins for such compositions include, but are not limited to polyurethanes, polyethylene glycol, epoxy resins, polyacrylates, polyamides, polyesters, polyacrylonitriles, cellulosics such as acetates, nitrates, and the like, phenolic resins, pentaerythritol resins, polyvinylpyrrolidone, polysaccharides, polyglucuronates, or co-polymers or blends of any two or more. The polymeric resin may be cured, or at least partially cured. As used herein, cured means that the resin is capable of undergoing a process that results in any one or more of hardening, polymerizing, thickening to provide a cured polymeric resin.

As with other materials containing the compounds of the specified formulas, inclusion of the compounds of Formula I, II, III, or a mixture of any two or more in the polymeric resin compositions causes a change in the refractive index, $\Delta\eta$, of the resin as compared to the resin without the compound(s). For example, $\eta$, may range from about 1 to about 2, from about 1.2 to about 1.95, from about 1.3 to about 1.9, or from about 1.33 to about 1.9, such as 1.52. In some embodiments, the addition of the compounds to a polymeric resin is referred to as doping of the polymer with the compound(s). Such doping includes where the compound(s) are present a level greater than about 1 ppm, in the polymer. The compound(s) may be present a level of up to and including 90%, when doped in a polymer. Therefore, doping, in some embodiments, includes where the compounds are present at a level of from about 1% to about 90%, in the polymer.

The compositions of the compound(s) in a polymeric resin may be formed, molded, or machined into various devices. Such devices may include includes a thin film of the compound of Formula I, II, III, or a mixture of any two or more on a substrate. Suitable substrates may include metal, glass, ceramics, and/or plastics.

Figure 2:
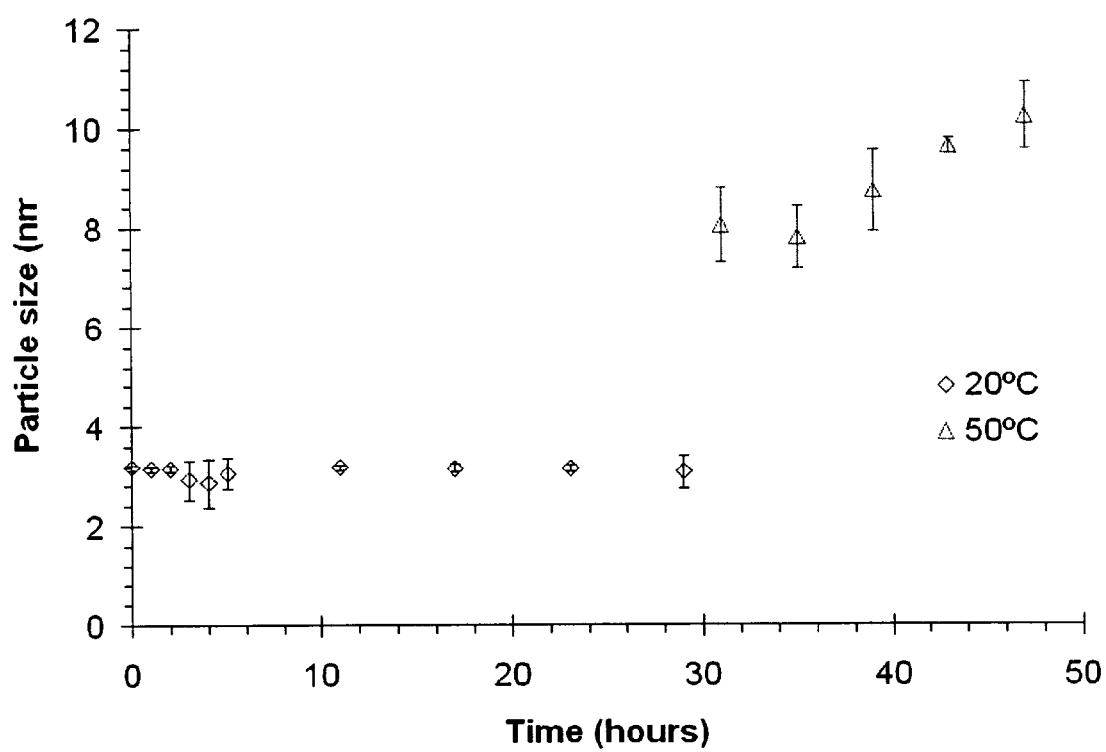
FIG. 2 is a graph of the growth kinetics obtained by dissolving bis(glycerol)oxotitanium (IV) and hydrolyzing it at various temperatures to make polyoxotitanates, according to one or more embodiments of the invention.
Figure 4:
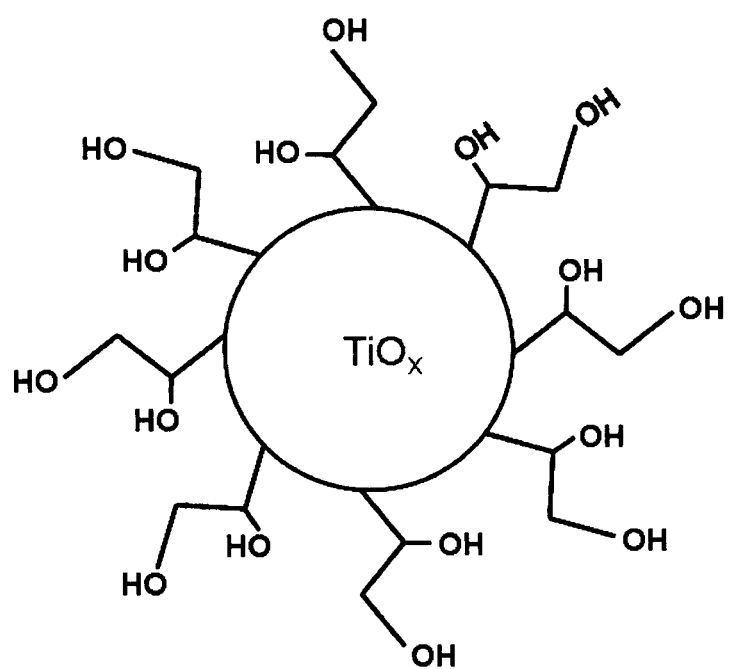
FIG. 4 is diagram of a titanium hydrosylate, according to one or more embodiments of the invention.

In some optional embodiments, a particle, nanoparticle, or organometallic polymer is formed from the compound of Formula I, II, III, or a mixture of any two or more thereof, as shown in FIG. 1. Methods of preparing a particle, nanoparticle, such as nanoparticulate $TiO_2$, include hydrolyzing the compound of Formula I, II, III, or a mixture of any two or more to form a hydrosylate, as depicted in FIG. 4. In some embodiments, the hydrosylate is a polyoxotitanate or a polyoxozirconate. In some embodiments, heat is used during the hydrolysis. Various parameters such as temperature, time, and addition rate, during the hydrolyzing step may be controlled, to prepare materials having a wide variety of properties from the hydrosylates. FIG. 2 is a graph showing growth kinetics obtained by dissolving the pure titanyl species and hydrolyzing it with heat to make polyoxotitanates. The hydrosylate typically is a mixture of polyoxotitanates that contain alkoxide moieties.

Figure 3:
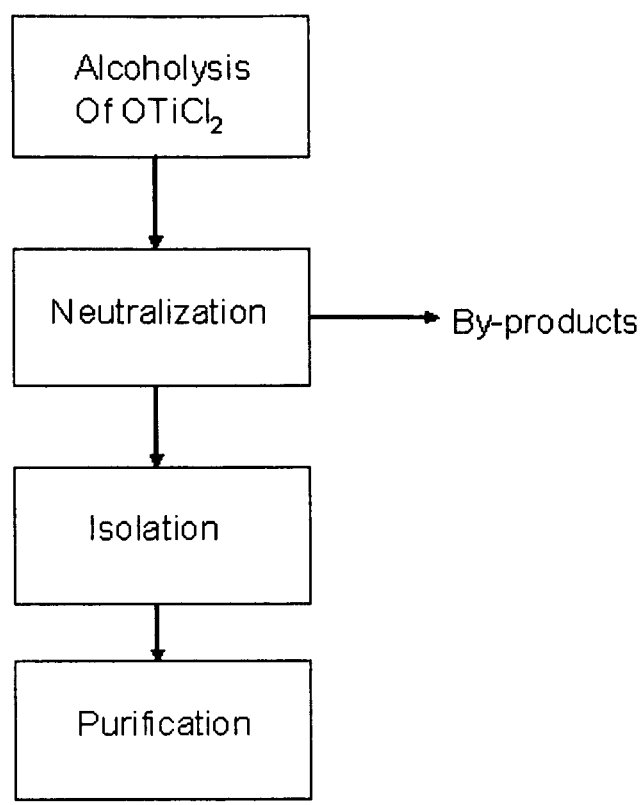
FIG. 3 is a flowchart diagram of the preparation of neutralized titanyl compounds as a powdered, pure chemical species, according to one or more embodiments of the invention.

The method of preparing a particle or nanoparticle may also include calcining of the hydrosylate, to prepare materials such as titania and zirconia. Particles and nanoparticles prepared by such methods may have a visible wavelength range transmittance of at least 90% and/or an ultra-violet light transmittance of less than about 20% in a wavelength range below about 400 nm. FIG. 3 is a flowchart describing the process of forming the neutralized titanyl compound as a powdered, pure chemical species. In some embodiments, the particles are a plurality of particles.

The organic and/or resulting nanoparticle compositions of a plurality of the particles described above, are suitable for a wide range of applications, including, but not limited to, refractive index modifier additives to optical devices, abrasion or scratch resistant coatings, coatings which provide a tunable mechanical hardness, UV blocking coatings, solar cell layers, paint additives, composite materials, such as a nanoparticle-polymer composite, etc. The compositions may be incorporated into a matrix material, such as a polymer layer, for uses such as the UV blocking and scratch resistant thin film on a glass window or windshield. However, the compositions retain their optical properties in the solid matrix, especially if the matrix material is optically transparent. If desired, the compositions may be incorporated into a gel or viscous liquid matrix, such as an optically clear sunscreen or cosmetic composition with UV absorbing properties. The compositions maintain their optical properties even in organic solvents, such as ethanol, methanol, toluene, etc., and thus can be incorporated into organic solvents and matrixes without substantial loss of optical properties.

Coating solutions are also provided having a composition of a plurality of nanoparticles formed by the methods described above dispersed in a first liquid and a second liquid. In such coating solutions, the first and second liquids each have a vapor pressure, however the vapor pressure of the second liquid is less than that of the first liquid. The first and second liquids are preferably miscible, but the nanoparticles are more compatible with the first liquid. As used herein, the phrase "more compatible" is defined as two liquids or materials which exhibit similar Hansen's 3-D solubility parameters. In some embodiments, the second liquid is a curable liquid, and in other embodiments, the second liquid is polymerizable. As used herein, the term "curable" may encompass polymerizable, but it also encompasses chemical phenomena such as crosslinking reactions induced by external radiative forces, and other curing methods known to those of skill in the art. Thus, the second liquid may be polymerized or cured by methods known to those of skill in the art, including, but not limited to heat, actinic radiation, electron beam radiation, moisture, or a combination of any two or more thereof. Such coating solutions may optionally include a crosslinker.

Suitable first liquids include, but are not limited to, water, organic solvents, inorganic solvents, and a mixture of any two or more thereof. Exemplary organic solvents include ketones, aromatic hydrocarbons, and a mixture of any two or more thereof.

Suitable second liquids include, but are not limited to water, organic solvents, inorganic solvents, and a mixture of any two or more thereof. Other suitable second liquids may include acrylates, methacrylates, epoxies, polyesters, polyols, isocyanates, polystyrene, polyacrylates, polymethacrylates, polyurethanes, and a mixture of any two or more thereof. Exemplary acrylates include isooctyl acrylate, 2-ethylhexyl acrylate, 1,6-hexanediol diacrylate, and a mixture of any two or more thereof. In some embodiments, the second liquid is 1-methoxy-2-propanol.

The coating solution may also include a material selected from dyes, pigments, fillers, electrically conductive particles, thermally conductive particles, fibers, film-forming polymers, catalysts, initiators, and a mixture of any two such materials. In some embodiments, the film-forming polymer is an adhesive. In other embodiments, the film-forming polymer is polymethylmethacrylate.

Also provided are methods of enhancing coating uniformity by applying the coating solution to a substrate surface, and removing at least a portion of the first liquid. The removing at least a portion of the first liquid may be accomplished by evaporation of the first liquid. In some embodiments, substantially all of the first liquid is removed. By having the different vapor pressures of the first and second liquids, such selective removal is enabled.

The methods may also further include removing at least a portion of the second liquid. The removing at least a portion of the second liquid may be accomplished by evaporation of the second liquid. In some embodiments, substantially all of the second liquid is removed.

In some embodiments, the method further includes curing and/or crosslinking the second liquid.

Devices of a substrate and a coating solution as described above may also be prepared. The substrate includes, but is not limited to glass, metal, polymer, wood, ceramic, paper, fabric, or a combination of any two or more thereof. In some specific embodiments, the substrate is an eyeglass lens, a camera lens, a binocular lens, a telescope lens, a mirror, a Fresnel lens, a compact disc, a DVD disc, a hologram, a window, a cellular phone, a personal data assistant, a calculator, a television, electronic paper, a computer privacy filter, or a computer touch screen.

Encapsulated solid state device may also be prepared. Such devices have a solid state device and an encapsulant, the encapsulant having (A) greater than about 40 wt % of a silicone epoxy resin, (B) between about 1 wt % and about 20 wt % of the hydrosylate as prepared above, (C) less than about 25 wt % of an anhydride curing agent, and (D) between about 0.008 wt % and about 10 wt % of an ancillary curing catalyst; and where the wt % amounts are based on the combined weight of (A), (B), (C) and (D). Optionally, the solid state device and the encapsulant may be in a package. In some embodiments, the solid state device is a semiconductor device. In other embodiments, the solid state device is an opto-electronic device. Exemplary opto-electronic devices include semiconductor devices such as integrated circuits, LEDs, CCDs, memory or logic devices, photodiodes, phototransistors, or opto-electronic couplers. In some embodiments, the package is a shell or lens.

As noted above, one of the components of the encapsulant may be a silicone epoxy resin. Such resins include, but are not limited to, a silicon moiety such as $R_3SiO_{0.5}$, $R_2SiO$, $RSiO_{1.5}$, and $SiO_2$; and/or an epoxy-containing silicone moiety of formula $EpR_2SiO_{0.5}$, $EpRSiO$, and $EpSiO_{1.5}$; where Ep is an epoxy moiety. The epoxy moiety may be a group selected from glycidoxypropyl, 3,4-epoxycyclohexane ethyl, and/or 1,2-epoxy hexyl; and R may be selected from hydrogen, alkyl, halogen-substituted alkyl, and/or aryl. In some cases, the silicone epoxy resin is 1,1,3,3-tetramethyl-1,3-bis[2(7-oxabicyclo[4.1.0]hept-3-yl)ethyl]disiloxane.

As noted above, the encapsulant may include an anhydride curing agent. Such anhydride curing agents may include bicyclo[2.2.1]hept-5-ene-2,3-dicarboxylic anhydride, methylbicyclo[2.2.1]hept-5-ene-2,3-dicarboxylic anhydride, bicyclo[2.2.1]hept-5-ene-2,3-dicarboxylic anhydride, phthalic anhydride, pyromellitic dianhydride, hexahydrophthalic anhydride, hexahydro-4-methylphthalic anhydride, dodecenylsuccinic anhydride, dichloromaleic anhydride, chlorendic anhydride, tetrachlorophthalic anhydride, or a mixture of any two or more such anhydrides. Ancillary curing agents may also be incorporated in the encapsulant and may include, but are not limited to, an organometallic salt, a sulfonium salt, an iodonium salt, or a mixture of any two or more. In some specific embodiments, the ancillary curing catalyst is a metal acetylacetonate, zinc octoate, stannous octoate, a metal carboxylate other than the metal acetylacetonate, zinc octoate and stannous octoate, triarylsulfonium hexafluorophosphate, triarylsulfonium hexafluoroantimonate, diaryliodonium hexafluoroantimonate, diaryliodonium tetrakis(pentafluorophenyl)borate, or a mixture of any two or more such materials. Optionally, the encapsulant may further include an additive such as thermal stabilizers, UV stabilizers, cure modifiers, coupling agents, refractive index modifiers, and a mixture of any two or more thereof. Exemplary UV stabilizers include hindered phenol stabilizers. Exemplary thermal stabilizers include phosphite stabilizers.

In other embodiments, the encapsulant is at least partially cured, and in some embodiments is cured.

In other aspects, the compounds described herein are useful as esterification catalysts, transesterification catalysts, and/or crosslinkers.

Owing to a broad range of applicability for such materials, the above compounds and compositions may be used in UV stabilizer systems for coatings. Such stabilizer systems may include a compound of Formula I, II, or III, a hydrosylate of a compound of Formula I, II, or III, or a titania or a zirconia particle made by any of the above methods, a substituted hydroxyphenyl-benzotriazole, and a hindered amine light stabilizer. The UV-light protective efficacy of the multicomponent system typically exceeds that of a system having the substituted hydroxyphenyl-benzotriazole and a hindered amine light stabilizer at the same levels, but without the added compounds or particles. Without being bound by theory, the combination of the above materials in the UV stabilizer system appears to have a synergistic effect over the additive properties of the components, individually, or in binary combinations. In other such embodiments, the suitable hydroxyphenyl-benzotriazoles are known to those of skill in the art and include, but are not limited to a number of the hydroxyphenyl-benzotriazoles in the Tinuvin®-class of compounds, and the like. Exemplary hydroxyphenyl-benzotriazole Tinuvin® compounds are those such as Tinuvin® P, TP, 99-2, 171, 384, 400, R-796, 900, 928, and 1130. In yet other such embodiments, hindered amine light stabilizers (HALs) are known to those of skill in the art, and include, but are not limited to a number of the HALs in the Tinuvin®-class of compounds, and the like. Exemplary HALs Tinuvin® compounds are those such as Tinuvin® 111, 123, 144, 152, 292, 292-HP, 622, and 5100. CHIMASORB 119 is another suitable HALs compound. In some embodiments, the hydrosylate or composition is present from less than 1 wt % to about 5 wt % or from about 0.5 wt % to about 4 wt %, or from about 1 wt % to about 3 wt %. In further embodiments, the hydroxyphenyl-benzotriazole is present from about 0.1 wt % to about 5 wt %, or from about 1 wt % to about 3 wt %; and the hindered amine light stabilizer is present from about 0.5 wt % to about 4 wt %, or from about 0.5 wt % to about 2 wt %. Such UV stabilizers may be used in a variety of paints and coatings known to those of skill in the art.

Desulfurization

In another aspect, the compounds may be used in processes to reduce the sulfur content of fuels. Reducing sulfur content in petroleum derived fuels has long been viewed as a means of mitigating air pollution from transportation exhaust. The refining industry typically employs hydrodesulfurization processes to remove thiols, sulfides, and disulfides from crude oil. However, refractory compounds such as dibenzothiophene and its derivatives require much more extreme conditions, such as high hydrogen pressures at elevated temperatures, to achieve ultra-low sulfur levels.

One alternative to hydrodesulfurization is oxidative desulfurization (ODS) combined with extraction. ODS of refractory compounds are based upon the susceptibility of such refractory compounds to oxidize to sulfoxides or sulfones under mild conditions, which may be removed by polar extractants. Oxidants such as nitrogen oxides, nitric acid, hydrogen peroxide, ozone, organic peroxides, oxygen, air, and peracids have been used. The oxidation of thiophene derivatives with hydrogen peroxide is known to take place in the presence of organic acid solvents such as $HCO_2H$, $CH_{3-x}Cl_xCO_2H$, $CF_3CO_2H$, and the like, where x is 0, 1, 2, or 3. Various catalysts and promoters studied, include sulfuric acid, tungstophosphoric acid (TPA), methyltrioxorhenium(VII), vanadium acetylacetonate, titanium molecular sieves, vanadium silicates, and many others. Unfortunately, many such solid-supported catalysts suffer from deactivation arising from metal leaching, sulfone adsorption, or combinations thereof. In addition, various extractants studied, include: polar volatile organic compounds (VOCs), expensive ionic liquids, and corrosive acids; some of which pose further environmental and safety concerns.

The compounds of Formula I, described above, may be used as catalysts for the reduction of sulfur or nitrogen level's in fuels. Without being bound by theory, it is believed that the compounds of formula I act to catalyze peracid formation in the reaction mixture. The peracid then oxidizes the sulfur or nitrogen species to sulfones or N-oxide species, respectively. The sulfones or N-oxide is then removed from the fuel by extraction with the bulk acid that is part of the reaction mixture.

Thus, in some embodiments, methods of using the compounds as sulfoxidation catalysts are provided. In such embodiments, a fuel source containing a sulfur containing refractive compound, or sulfur contaminant, is mixed with an appropriate solvent and an aliquot of a solution of a compound of formula I is added. In other embodiments, methods of using the compounds as nitrogen oxidation catalysts are provided. In such embodiments, a fuel source containing a nitrogen-containing contaminant is mixed with an appropriate solvent and an aliquot of a solution of a compound of formula I is added. Both sulfur and nitrogen contaminants may be present in the same fuel and may be treated with the same catalyst compositions.

Suitable fuel sources are any sulfur- or nitrogen-contaminated fuel source including, but are not limited to, crude oil, diesel fuels, and thermally cracked gasolines such as gasoline, visbreaker gasoline, coker gasoline and catalytically cracked gasoline. As used herein, the phrase "cracked gasolines" refers to any of a number of fuels formed by thermally degrading higher molecular weight hydrocarbons over catalysts. Such cracking catalysts and processes are well-known in the art and are routinely used in the production of fuels sources.

As used herein, the term contaminant refers to any amount of an undesired compound, or compounds in a fuel, such as compounds that contain sulfur or nitrogen. Also, as used herein, decontaminated refers to a reduction in contaminant level in a product compared to the level of contaminant before treatment. Thus, decontaminated does not necessarily mean that all contaminants are eliminated, although it can include complete decontamination, but rather, decontaminated means that the amount of contaminant is reduced, as compared to the fuel prior to a decontamination treatment. In some embodiments, decontaminated fuels have at least a 10% reduction in contamination as compared to the contaminated fuel that is provided. In other embodiments, the reduction may variously be at least 20%, at least 30%, at least 40%, at least 50%, at least 60%, at least 70%, at least 80%, at least 90%, or even as high as 100%.

Sulfur-containing refractive compounds include, but are not limited to mercaptans, sulfides, disulfides, thiophene, benzothiophene (BT), alkyl benzothiophenes, dibenzothiophene (DBT), 4-methyldibenzothiophene (4-MDBT), alkyl dibenzothiophenes such as 4,6-dimethyldibenzothiophene (DMDBT), organic sulfur compounds of alkylnapthalenes, and derivatives of such compounds.

Nitrogen-containing contaminants include, but are not limited to nitrogen heterocyles. For example, such nitrogen heterocycles include but are not limited to carbazole, imidazole, triazoles, benzotriazoles, quinuclidine, aziridine, azetidine, pyrrolidine, pyrazolidine, pyrrole, pyrrolidine, pyrazole, tetrazoles, piperidine, piperazine, morpholine, pyridine, pyrimidine, pyridazine, triazine, dihydropyridine, indole, indolines, isoindoles, azaindoles, indazole, indolizine, benzotriazole, benzimidazole, pyrazolopyridine, azabenzimidazolyl, triazolopyridine, isoxazolopyridine, purine, adenine, guanine, quinoline, isoquinoline, quinolizine, quinoxaline, quinazoline, phthalazine, naphthyridine, pteridine, dihydroindole, tetrahydroindole, tetrahydroindazole, tetrahydrobenzimidazole, tetrahydrobenzotriazole, tetrahydropyrrolopyridine, tetrahydropyrazolopyridine, tetrahydroimidazopyridine, tetrahydrotriazolopyridine, and tetrahydroquinoline, and derivatives thereof. Suitable solvents for sulfoxidation include, but are not limited to organic acid solvents such as $HCO_2H$, $CH_{3-x}Cl_xCO_2H$, $CF_3CO_2H$, and the like, where x is 0, 1, 2, or 3.

Methods of decontaminating fuels, according to some embodiments, include preparing a mixture of a sulfur- and/or nitrogen-contaminated fuel, a compound of formula I, an organic acid; and an oxidant; and recovering the decontaminated fuel. A number of examples are provided below in which oils are prepared having a sulfur or nitrogen content, in the form of benzothiophenes and carbazole, and in which the present compounds are used as catalysts to decontaminate the oil under experimental conditions. By such control of the conditions, the effectiveness of the catalysts may be determined and monitored.

According to some embodiments, the catalyst used for the desulfurization is bis(ethyleneglycol)oxotitanium (IV), bis(glycerol)oxotitanium (IV), bis(erythritol)oxotitanium (IV), bis(sorbitol)oxotitanium (IV), or a mixture of any two or more such compounds or cluster compounds.

The organic acid that is used, may be one that is known in the art for use with other such catalyst systems. For example, the organic acid may be $HCO_2H$, $CH_{3-x}CCl_xCO_2H$, $CF_3CO_2H$, and mixtures of any two or more such acids, where x is 0, 1, 2, or 3. Likewise the oxidant that is used may be a material such as organic nitrogen oxides, nitric acid, hydrogen peroxide, a bleach such as sodium hypochlorite, ozone, organic peroxides, oxygen, air, peracids, and mixtures of any two or more such compounds. Depending upon the fuel and other reactants, the amount of organic acid used in ratio to the amount of fuel can range from 1:1 on up. In some embodiments, the ratio of acid to fuel is 1:1, 4:1 in other embodiments, or about 10:1 in yet other embodiments.

As used herein, the term organic peroxides refers to organic groups have a peroxide functionality of formula RC(O)OOC(O)R', where R and R' are individually alkyl, alkenyl, alkynyl, aryl, cyclyl, heterocyclyl, or heteroaryl groups. Such compounds may include, but are not limited to benzoyl peroxide. As used herein, the term organic nitrogen oxide refers to organic compounds that are substituted with an NO group, such as, but not limited to pyridine N-oxide, morpholine N-oxide. As used herein, the term peracids refers to any organic acids have a peroxo functionality for formula R"C(O)OOH, where R" is alkyl, alkenyl, alkynyl, aryl, cyclyl, heterocyclyl, or heteroaryl group. Such peracids are defined as carboxylic acids that have been treated with hydrogen peroxide to form a species of general formula R"C(O)OOH. Examples of such peracids include, but are not limited to performic, peracetic acid, pertrifluoroacetic acid, and the like.

The ratios of the components used in the decontamination reactions to desulfurize or denitrogenate fuels may be varied to optimize for a particular catalyst, acid, oxidant, or temperature. Thus, in some embodiments, the amount of fuel in the mixture of reactants may vary from about 30 to 70 wt %, or from about 40 to 60 wt % in other embodiments. In some embodiments, the organic acid is present from about 20 to 60 wt %, or from about 25 to 40% in other embodiments. The organic acid is reacted with the oxidant to form a peracid species that is the oxidation source for the sulfur or nitrogen contaminants, but the organic acid also acts as the extractant to remove the sulfones or nitrogen oxide from the fuel.

The oxidant level is typically based upon the mole ratio to the sulfur or nitrogen contaminant present. It may be expected that the desired ratio or oxidant to sulfur is 1:1 on a per mol basis, however higher loadings up to 3:1 or even to 8:1 may be necessary to achieve the desired kinetic profile. In some embodiments, the oxidant is present in the mixture from about 5 to 20 wt %, or from about 10 to 18 wt %, in other embodiments.

Generally, the lower the catalyst loading to achieve the desired efficiency the better in terms of cost. However, the catalyst loading may vary widely. The catalyst may be present in the mixture from about 0.02 to 0.8 wt %, according to some embodiments, or from about 0.04 to 0.4 wt %, in other embodiments. In other embodiments, the catalyst is present in a ratio of 0.5 ppm or greater with respect the fuel.

In one particular embodiment, the catalyst is eliminated and a hypochlorite, such as sodium hypochlorite, is used as the oxidant. In such a case, the action of the hypochlorite on the organic acid such as acetic acid produces a peracid species capable of oxidizing the sulfur to a sulfone, that is then removed from the fuel mixture.

Temperature of the reaction and time also play a role in catalyst efficiency and reaction kinetics. The temperature may range from ambient temperature on up. The upper limit is bounded by the desire to keep the reactant in the reactor and to not lose reactants and/or products due to overheating. Thus, in some embodiments, the methods are conducted at ambient temperature. However, in other embodiments, the temperature of the reaction may range from about 30 to 130° C., or from about 40 to 60° C. Consideration is also given to the time of the reaction. In an isolated reactor this is simply how long the reaction is run before process, however in online systems, time is determined as residence time in the reactor. Such time may vary depending upon reactants, contaminant level or a number of other factors known to those of skill in the art. In some embodiments, the time ranges from about 5 seconds to 60 minutes. While in other embodiments, the time ranges from about 1 minute to 30 minutes, or from about 1 minute to 10 minutes.

Figure 8:
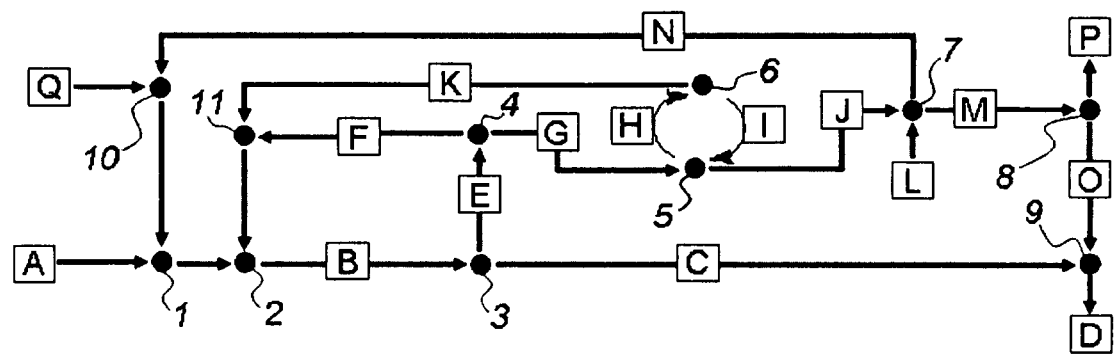

FIG. 8 is a process flow diagram of an embodiment of a sulfoxidation process such as those described above. Source A may comprise a sulfur-rich organic fluid stream input into the process at mixing point 1, where the organic fluid may be a fluid such as those described above. Source Q may comprise an oxidant introduced into the system at reactor 10, where the oxidant may comprise oxidants described above, where the oxidant mixes with the organic fluid stream at mixing point 1. Source Q may comprise an electric input in embodiments where the oxidant is produced by hydrolysis.

The mixture from mixing point 1 may be combined with a catalyst in reactor 2 to form a biphasic oil-reaction mixture, resulting in the sulfoxidation of the sulfur-rich organic fluid within reactor 2, where oxidized sulfur compounds are extracted from the organic fluid phase into an aqueous reaction phase. The catalyst may be those described above. The catalyst may enter the reactor 2 as a solid or liquid, and may be transferred to reactor 2 from mixing point 11. In some embodiments, the mixing performed at mixing points 1 and 11 may be performed at reactor 2.

A biphasic oil-reaction stream B may be transferred from reactor 2 to separator 3, where a sulfur-rich polar extractate E may be separated from low-sulfur (or essentially sulfur-free) raffinate C. The sulfur-rich extractate E (comprising oxidized sulfur compounds and catalyst) may be transferred from the separator 3 to a distillation tower 4, where distillate overheads F (pure extractant, such as solvent) may be separated via distillation from distillate heavies G, where distillate heavies may comprise oxidized sulfur compounds (such as organic sulfones) and catalyst. Distillate overheads F may be returned to mixing point 11. In some embodiments, the sulfur-rich extractate E may represent about 15% of the biphasic oil-reaction stream B and the low-sulfur (or essentially sulfur-free) raffinate C may represent about 85% of the biphasic oil-reaction stream B.

Distillate heavies G may be transferred to extractor 5, where catalyst may be extracted through process H using distillation tower 6, and solvent may be returned to extractor 5 through process I. Catalyst concentrate K may be returned to mixing point 11. The remaining sulfur-rich, salt-containing heavies J may be transferred from extractor 5 to extractor 7, where salts may be removed through aqueous wash output N and returned to reactor 10. Where the oxidant is NaOCl, the process at extractor 7 may comprise a salt extraction. Extractor 7 may comprise a solvent wash when other oxidants are used. Water may be introduced into extractor 7 through input L.

The sulfur rich heavies M (e.g., sulfur-rich organics) may be transferred from extractor 7 to reactor 8. Reactor 8 may comprise a high temperature reactor and may utilize a catalyst, such as a solid bed catalyst. At reactor 8, the sulfur rich heavies may be catalytically fractioned into $SO_2$ and organic compounds, where $SO_2$ may be removed from reactor 8 at $SO_2$ output P. Recovered organic compounds O produced in reactor 8 (e.g. oil, etc.) may be transferred from reactor 8 to mixing point 9 where the organic compounds O are mixed with the low-sulfur raffinate C and may be transferred to low-sulfur gas oil output D.

One skilled in the art will readily realize that all ranges and ratios discussed can and do necessarily also describe all subranges and subratios therein for all purposes and that all such subranges and subratios also form part and parcel of this invention. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention will be better understood by reference to the following example which is intended for the purpose of illustration and is not intended to nor is to be interpreted in any way as limiting the scope of the present invention, which is defined in the claims appended hereto.

EXPERIMENTAL

Example 1

Preparation of bis(glycerol)oxotitanium(IV). Titanium oxychloride (2 kg, Millennium Chemicals) was diluted with de-ionized water (2 Kg) and then added to a 20 L round bottom flask containing glycerin (2 kg). The mixture was allowed to stir until a straw color was attained. The 20 L round bottom flask was then heated to 50° C. under vacuum (−25 in Hg) in a rotary evaporator to remove excess water and hydrochloric acid. When no further liquid condensate was noted, the flask was recharged with water (0.65 L) and rotary evaporated to further remove excess water and hydrochloric acid. This was repeated 2 additional times. After the final evaporation, the viscous, straw colored liquid was weighed (2.64 kg) and diluted with methoxypropanol (0.85 kg) to reduce the viscosity. This was then neutralized with triethylamine (3.3 kg, 33% w/w in ethanol). The combined neutralized solution was then chilled for several hours producing rod-like needles of triethylamine hydrochloride. The crystalline triethylamine hydrochloride was removed by vacuum filtration. The filtrate was added slowly to acetone (70 L) causing the product to precipitate as a white solid. The acetone was then decanted and an off-white solid residue was obtained. The off-white solid residue was then washed vigorously with hexanes (20 L) to afford a fine white powder. The powder was collected by filtration (>63% yield based upon Ti). % Ti Calculated: 16.98. Analysis: 16.7; mp DSC (dec) 273° C.; ESI-MS (positive mode) 245 amu; $^1$H-NMR (DMSO-d6) 4.25 (br s, 4H), 3.45 (m, 2H), 3.38 (m, 4H), 3.31 (m, 4H).

Example 2

Preparation of bis(ethyleneglycol)oxotitanium(IV). Titanium oxychloride (100.75 g, Millennium Chemicals) was diluted with de-ionized water (100.15 g) and then added to a 1 L round bottom flask containing ethylene glycol (59.7 g, VWR). The mixture was allowed to stir until a faint grey color was attained. The 1 L round bottom flask was then heated to 65° C. under vacuum (−25 in Hg) in a rotary evaporator to remove excess water and hydrochloric acid. When no further liquid condensate was noted, the flask was recharged with water (50 mL) and rotary evaporated to further remove excess water and hydrochloric acid. This was repeated 2 additional times. After the final evaporation, the viscous, clear liquid was weighed (90.3 g).

Example 3

Preparation of bis(diethyleneglycol monobutylether)oxotitanium(IV) [(BuO(CH$_2$)$_2$O(CH$_2$)$_2$O)$_2$TiO]. Titanium oxychloride (17.6 g, Millennium Chemicals) was diluted with de-ionized water (17.6 g) and then added to a 1 L round bottom flask containing diethyleneglycol monobutylether (15 g, VWR). The mixture was allowed to stir until a faint orange color was attained. The 1 L round bottom flask was then heated to 65° C. under vacuum (−25 in Hg) in a rotary evaporator to remove excess water and hydrochloric acid. When no further liquid condensate was noted, the flask was recharged with water (50 mL) and rotary evaporated to further remove excess water and hydrochloric acid. This was repeated 2 additional times. After the final evaporation, the viscous, yellow oil was weighed (22 g). $^1$H-NMR (DMSO-$d_6$) 4.19 (br s, 6H), 3.45-3.39 (m, 12H), 3.37-3.34 (m, 4H), 3.31 (m, 4H), 1.41 (m, 4H), 1.24 (m, 4H), 0.81 (t, 6H).

Example 4

Preparation of polymers. Bisglycerolato-oxotitanium(IV) was dissolved in dimethyl sulfoxide (DMSO) at a loading of 10 wt % solids. 2 mL of this solution was added to 2 mL of distilled water and agitated to ensure a homogeneous starting solution. The resultant solution was placed in a quartz cuvette which had been rinsed three times with distilled water filtered through a 0.2 μm PTFE filter. The cuvette was placed in a particle size analyzer. Initially the temperature was held constant at 20° C. and the particle size measured at regular intervals. After 29 hours the temperature was increased to 50° C. and held constant at that value and again particle size measurements were taken at regular intervals. The particle size data shows no change in particle size during the time at 20° C. but shows a steadily increasing particle size during the time at 50° C.

Desulfurization Examples

The process of conducting sulfoxidation with the compounds of formula I is generally described above, will be better understood by way of the following general methods and examples.

Example 5

Three general methods were used to prepare various samples. Each involved the preparation of a model oil by dissolving dibenzothiophene (DBT) in tetralin to give solutions with a sulfur content of about 15,000 parts per million (ppm) (approximately 0.76 grams of DBT dissolved in 8.33 grams of tetralin). A heated circulating bath was used to control the temperature (±0.1K) of the reactor (J-KEM), at approximately 323 K, for the elevated temperature samples. Aliquots of the oil phase were withdrawn at various time intervals and measured by chromatographic techniques for extent of conversion of the DBT. The reactions were stirred with a mixing bar speed of about 200 revolutions per minute (rpm).

General Method A. Catalyst solutions were prepared of 40 wt % bis(glycerol)oxotitanium (IV) in methanol. The oxidative desulfurization experiments were then carried out by combining acetic acid with the model oil in a glass batch reactor, adding a measured aliquot of the catalyst solution and then adding a quantity of the oxidant.

General Method B. The oxidative desulfurization experiments were carried out by combining acetic acid and the solid catalyst, bis(glycerol)oxotitanium (IV), with the model oil in a glass batch reactor, and then adding a measured quantity of the oxidant.

General Method C. The oxidative desulfurization experiments were carried out by combining acetic acid and a measured aliquot of a 40% by weight solution of bis(glycerol)oxotitanium (IV) in methanol with the model oil in a glass-lined pressure reactor. Reaction time started upon pressurization with air.

Analytical Methods

HPLC was carried out using an HP 1090 liquid chromatograph fitted with column oven and a diode array detector. The system was controlled and data collected using an HP Chemstation V.5.03. The column was a Phenomenex Luna (2) C-18 column 250×4.6 mm. The column oven was held at 40° C. The solvents contained of acetonitrile (J. T. Baker HPLC Grade Acetonitrile part #9017-03) and Milli-Q water. The solvent program was 50% solvent A, balance B, with a ramp to 100% solvent A at 20 minutes and a 2 minute hold. On returning to start conditions there was an equilibration delay of 8 minutes before injection of the next sample. The flow rate was 1.0 mL/min and the injection volume was 10 μl. The diode array detector was set at 260 nm (decalin) and 325 nm (tetralin) with bandwidths of 4 nm. Identification of starting materials and reaction products was aided by comparison of retention times to commercial standards. A five point calibration curve was used to derive analyte concentrations, percent yield values describe percent consumption of the benzothiophene starting material.

NMR experiments were conducted on a Varian VNMRS-500 in d8-toluene unless otherwise noted. The spectra of styrene oxide and trans-stilbene oxide were obtained on commercially available materials and used for comparison to the oxidation product spectra.

Desulfurization

Figure 6:
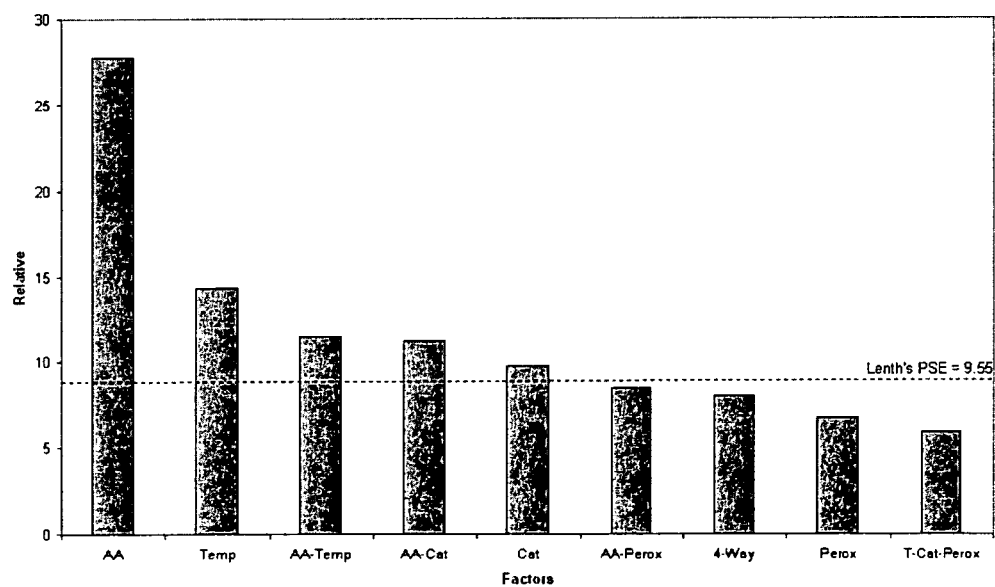
FIG. 6 is a Pareto analysis graph of samples 1-18 (AA=Acetic Acid, Temp=temperature, Cat=catalyst loading, Perox=peroxide strength).

Reactions were run varying catalyst loading (Cat. Vol.), oxidant strength (Oxidant, $H_2O_2$ concentration), acid strength (Acid, 25% acetic vs. Glacial Acetic), and temperature (T) according to General Method A and analyzed for percent conversion (% yield) after 1 hour. The catalyst was a 40 wt % methanol solution of bis(glycerol)oxotitanium (IV). The volume of acid was between about 8.35 and about 8.37 g. The amount of oxidant was about 2.80 g. The results obtained are shown below in Table 1 and in FIG. 6.

TABLE 1

Desulfurization Results

| Sample | Cat. Vol. | Acid | Oxidant | T | % yield |
|---|---|---|---|---|---|
| 1 | 10 μl | 25% acetic | $H_2O_2$ (25%) | RT | 0 |
| 2 | 10 μl | 25% acetic | $H_2O_2$ (25%) | 50° C. | 16.6 |
| 3 | 10 μl | 25% acetic | $H_2O_2$ (50%) | RT | 0 |
| 4 | 10 μl | 25% acetic | $H_2O_2$ (50%) | 50° C. | 1.4 |
| 5 | 100 μl | 25% acetic | $H_2O_2$ (25%) | RT | 0.2 |
| 6 | 100 μl | 25% acetic | $H_2O_2$ (25%) | 50° C. | 1.9 |
| 7 | 100 μl | 25% acetic | $H_2O_2$ (50%) | RT | 0.3 |
| 8 | 100 μl | 25% acetic | $H_2O_2$ (50%) | 50° C. | 3.6 |
| 9 | 10 μl | Glacial acetic acid | $H_2O_2$ (25%) | RT | 3.9 |
| 10 | 10 μl | Glacial acetic acid | $H_2O_2$ (50%) | 50° C. | 96.4 |
| 11 | 10 μl | Glacial acetic acid | $H_2O_2$ (50%) | RT | 9 |
| 12 | 10 μl | Glacial acetic acid | $H_2O_2$ (25%) | 50° C. | 40.9 |
| 13 | 100 μl | Glacial acetic acid | $H_2O_2$ (25%) | RT | 28.3 |
| 14 | 100 μl | Glacial acetic acid | $H_2O_2$ (25%) | 50° C. | 100 |
| 15 | 100 μl | Glacial acetic acid | $H_2O_2$ (50%) | RT | 89.8 |
| 16 | 100 μl | Glacial acetic acid | $H_2O_2$ (50%) | 50° C. | 100 |
| 17 | 100 μl | Glacial acetic acid | $H_2O_2$ (50%) | 50° C. | 100 |
| 18 | 100 μl | Glacial acetic acid | $H_2O_2$ (50%) | 50° C. | 100 |

Sample 19. Due to the 100% yield result of Sample 16, the same conditions were repeated an aliquots drawn at 10 minute intervals for 40 minutes. The results obtained are shown below in Table 2:

TABLE 2

Yield Results at time, t, for 100 μl catalyst volume, in glacial acetic acid, 50% $H_2O_2$, at 50° C.

| t (min.) | % Conversion |
|---|---|
| 10 | 63.4 |
| 20 | 98.8 |
| 30 | 100 |
| 40 | 100 |

Sample 20. Sample 19 conditions were repeated, but with a reactor agitator spin rate of 400 rpm. Aliquots were withdrawn for analysis at 5, 15, and 25 minutes to measure the effect. The results obtained are shown below in Table 3.

TABLE 3

Faster Agitator Spin Rate Results

| t (min) | % Conversion |
|---|---|
| 5 | 50.6 |
| 15 | 99.2 |
| 25 | 100 |

Sample 21. The conditions of Sample 20 were repeated, however the mass ratio of glacial acetic acid to tetralin was doubled. Aliquots were withdrawn for analysis at 5, 10, and 12 minutes to measure the effect. The results obtained are shown below in Table 4.

TABLE 4

Higher Glacial Acid to Tetralin Ratio.

| t (min) | % Conversion |
|---|---|
| 5 | 99.3 |
| 10 | 100 |
| 12 | 100 |

Sample 22. The conditions of Sample 21 were repeated, however the concentration of hydrogen peroxide was reduced to 3 mole equivalents with respect to DBT. Aliquots were withdrawn for analysis at 5, 15, and 25 minutes to measure the effect. The results obtained are shown below in Table 5.

TABLE 5

Hydrogen Peroxide at 3 Equivalents.

| t (min) | % Conversion |
|---|---|
| 5 | 84.4 |
| 15 | 100 |
| 25 | 100 |

Samples 23-39. Reactions were run varying the amount of catalyst volume (Cat. Vol.), oxidant level (Oxidant, $H_2O_2$ concentration), acid strength (Acid, 25% acetic vs. Glacial Acetic), and temperature (T) according to General Method B and analyzed for percent conversion (% yield) after 1 hour. RT is defined as a room temperature of approximately 20° C. The catalyst was solid bis(glycerol)oxotitanium(IV) (limited solubility in acetic acid). The amount of acid was between about 8.34 and about 8.38 g. The amount of oxidant was about 2.80 g. The results are shown below in Table 6.

TABLE 6

Desulfurization by General Method B.

| Sample | Acid | wt Ox | T | % yield |
|---|---|---|---|---|
| 23 | 25% acetic | 8.6 mg $H_2O_2$ (25%) | 50° C. | 0 |
| 24 | Glacial acetic acid | 8.5 mg $H_2O_2$ (25%) | 50° C. | 84.9 |
| 25 | 25% acetic | 84.5 mg $H_2O_2$ (25%) | 50° C. | 3.5 |
| 26 | Glacial acetic acid | 84.1 mg $H_2O_2$ (25%) | 50° C. | 100 |
| 27 | 25% acetic | 8.4 mg $H_2O_2$ (50%) | 50° C. | 1.3 |
| 28 | Glacial acetic acid | 8.5 mg $H_2O_2$ (50%) | 50° C. | 99.2 |
| 29 | 25% acetic | 83.7 mg $H_2O_2$ (50%) | 50° C. | 2.7 |
| 30 | Glacial acetic acid | 83.5 mg $H_2O_2$ (50%) | 50° C. | 100 |
| 31 | Glacial acetic acid | 84.0 mg $H_2O_2$ (50%) | 50° C. | 100 |
| 32 | 25% acetic | 8.6 mg $H_2O_2$ (50%) | RT | 0 |
| 33 | Glacial acetic acid | 8.6 mg $H_2O_2$ (25%) | RT | 11.6 |
| 34 | 25% acetic | 84.6 mg $H_2O_2$ (25%) | RT | 0 |
| 35 | Glacial acetic acid | 84.4 mg $H_2O_2$ (25%) | RT | 92.9 |
| 36 | 25% acetic | 8.4 mg $H_2O_2$ (25%) | RT | 0 |
| 37 | Glacial acetic acid | 8.4 mg $H_2O_2$ (50%) | RT | 21 |
| 38 | 25% acetic | 84.3 mg $H_2O_2$ (50%) | RT | 0.5 |
| 39 | Glacial acetic acid | 84.7 mg $H_2O_2$ (50%) | RT | 95.9 |

Catalyst Effect on Nitrogen-Containing Organics

Petroleum distillates are complex mixtures and often contain olefin and nitrogen-containing heterocycles. Experiments were also performed employing styrene and trans-stilbene and carbazole to model the effect of the catalysts on olefin and nitrogen heterocycles in fuels. The model carrier employed was $d_8$-toluene so that analysis could be conducted by NMR spectroscopy. Under the reaction conditions and times described above, no styrene oxidation products were noted. Trans-stilbene did not show any oxidation at 15 minutes and ~13% oxidation to trans-stilbene oxide was noted after 1 hour. The complete oxidation of carbazole was noted within 15 minutes as evidenced by the disappearance of the N—H proton resonance.

A model oil was prepared by independently dissolving an olefin (styrene and trans-stilbene) to 10% by weight in $d_8$-toluene (6 grams). The oxidation experiments were carried out by combining acetic acid (18 g) with the model oil in a glass batch reactor, adding 100 μL of a 40% by weight solution of bis(glycerol)oxotitanium (IV) in methanol and then adding 5 mole equivalents of 50% $H_2O_2$ solution (olefin basis). The reactor was mixed at an agitator rate of 200 rpm. A heated circulating bath was used to control the temperature (±0.1K) of the reactor (J-KEM), at 323 K. The experiment was run for an hour with aliquots pulled at 15 minutes and 1 hour for conversion. After 15 minutes no oxidation was noted for either olefin by $^1$H- and $^{13}$C-NMR analysis. After 1 hour, no oxidation was observed for styrene and only partial epoxidation (13%) was noted for trans-stilbene after 1 hour.

A model oil was prepared by dissolving carbazole (10%) in d8-toluene (6 grams). The oxidation experiment was carried out by combining acetic acid (18 g) with the model oil in a glass batch reactor, adding 100 μL of a 40% by weight solution of bis(glycerol)oxotitanium (IV) in methanol and then adding 5 mole equivalents of 50% $H_2O_2$ solution (olefin basis). A heated circulating bath was used to control the temperature (±0.1K) of the reactor (J-KEM), at 323 K. The experiment was run for an hour with aliquots pulled at 15 minutes and 1 hour for conversion. After 15 minutes complete oxidation was noted for carbazole as evidenced by disappearance of the N—H stretch by $^1$H-NMR.

Figure 7:
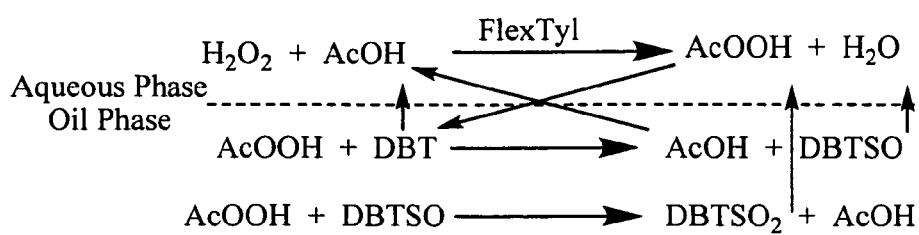
FIG. 7 is a scheme of potential oxidation reactions and relevant mass transfers and FIG. 8 is a process flow diagram of an embodiment of a sulfoxidation process.

The reactions occurring in the process presumably involve formation of peracetic acid catalyzed by the compounds of Formula I. Peracetic acid has cross-solubility into the oil phase and can react with DBT to form sulfoxides. The sulfoxides have cross-solubility with the acetic acid phase and can be further oxidized to the sulfone which has a greater affinity for the acetic acid phase. The reactions and mass transfers are displayed graphically in FIG. 7.

Desulfurization Kinetics

A model oil was prepared by dissolving DBT (72.4 mg, 0.39 mmoles), benzothiophene (BT) (54.1 mg, 0.4 mmoles), 4-methyldibenzothiophene (4-MDBT) (81.0 mg, 0.41 mmoles), and 4,6-dimethyldibenzothiophene (DMDBT) (78.5 mg, 0.37 mmoles) in decalin. The oxidation experiment was carried out by combining acetic acid (12 g) with the model oil in a glass batch reactor, adding 100 μL of a 40% by weight solution of bis(glycerol)oxotitanium (IV) in methanol and then adding 2.8 grams of 50% $H_2O_2$ solution (26:1 O:S ratio). The reactor was mixed at an agitator rate of 200 rpm. A heated circulating bath was used to control the temperature (±0.1K) of the reactor (J-KEM) at approximately 323 K. The experiment was run for a half hour with aliquots pulled at 5, 15, and 30 minute intervals (full phase separation was allowed to occur at which point sampling was taken and time noted). The kinetic data shown in FIG. 5 are plotted in comparison to the results of tungstophosphoric acid as determined by Yazu et al. *Chemistry Letters* 32(10), 920 (2003).

Figure 5:
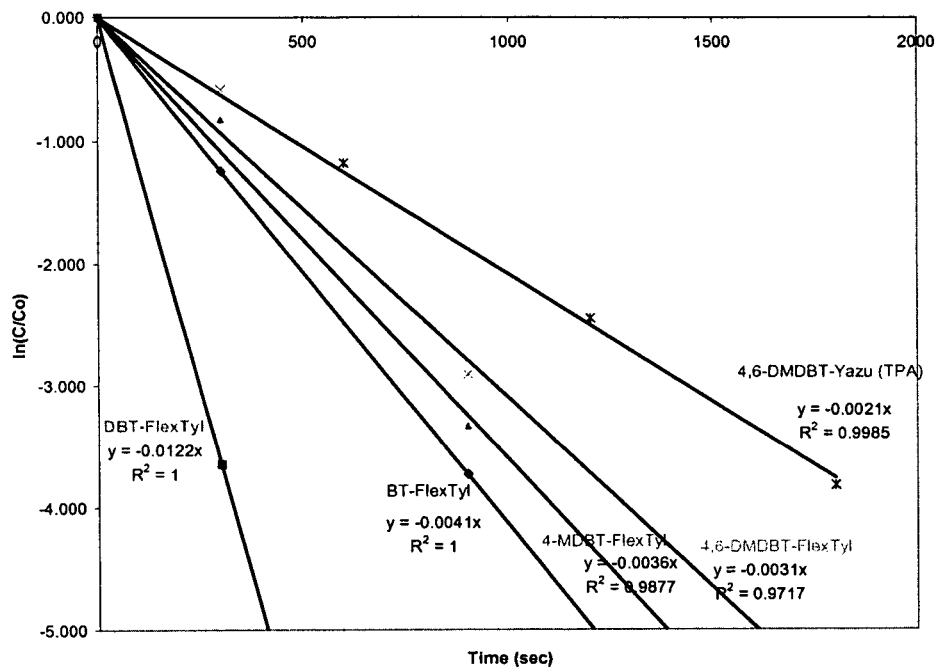
FIG. 5 is a pseudo-$1^{st}$ order plot for the oxidation of benzothiophenes (26:1 Oxidant:S ratio, 9700 S:Ti ratio, 2 Acetic Acid:Oil mass ratio).

As shown in FIG. 5, the disappearance of DBT and its derivatives are pseudo first order in excess peroxide and acetic acid conditions. As can be seen, the oxidation rates follow the order DBT>BT>MDBT>DMDBT. In contrast, the rates for DBT and DMDBT observed by Yazu were identical.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

What is claimed is:

1. A compound of formula I: $M_mO_m(OR^2)_n$ (I):
wherein;
M is Ti, Zr, or Hf;
$R^2$ at each occurrence is individually a substituted alkyl group containing at least one OH group, a substituted cycloalkyl group containing at least one OH group, a substituted cycloalkylalkyl group containing at least one OH group, a substituted heterocyclyl group containing at least one OH group, or a heterocyclylalkyl containing at least one OH group; and
m is an integer from 1 to 8;
n is an integer from 1 to 8;
wherein, the compound of formula I is a compound of formula II

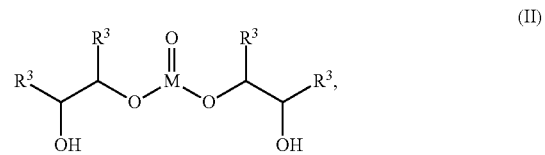

a compound of formula III

an isomer of the compound of Formula II, III, or a mixture thereof, wherein:

$R^3$ at each occurrence is independently H, F, Cl, Br, I, CN, $OR^4$, $NR^5R^6$, substituted or unsubstituted alkyl, substituted or unsubstituted cycloalkyl, substituted or unsubstituted cycloalkylalkyl, unsubstituted heterocyclyl, or substituted or unsubstituted heterocyclyl alkyl;

$R^4$ is H, substituted or unsubstituted alkyl, substituted or unsubstituted cycloalkyl, substituted or unsubstituted cycloalkylalkyl, unsubstituted heterocyclyl, or substituted or unsubstituted heterocyclylalkyl;

$R^5$ and $R^6$ are independently H, substituted or unsubstituted alkyl, substituted or unsubstituted cycloalkyl, substituted or unsubstituted heterocyclylalkyl, or $R^5$; and n' is 0, 1, 2, 3, or 4.

2. The compound of claim 1, wherein M is Ti.

3. The compound of claim 1, wherein $R^3$ at each occurrence is independently H, $OR^4$, or a substituted or unsubstituted alkyl group.

4. The compound of claim 1, wherein the compound is bis(ethyleneglycol)oxotitanium (IV), bis(glycerol)oxotitanium (IV), bis(erythritol)oxotitanium (TV), or bis(sorbitol) oxotitanium (IV).

5. The compound of claim 1, having a visible wavelength range transmittance of at least 90%.

6. The compound of claim 1, having an ultra-violet light transmittance of less than about 20% in a wavelength range below about 400 nm.

* * * * *